United States Patent
Thorp et al.

[11] Patent Number: 5,968,745
[45] Date of Patent: Oct. 19, 1999

[54] POLYMER-ELECTRODES FOR DETECTING NUCLEIC ACID HYBRIDIZATION AND METHOD OF USE THEREOF

[75] Inventors: H. Holden Thorp, Chapel Hill; Carson R. Loomis, Durham; Mary E. Napier, Carrboro, all of N.C.

[73] Assignees: The University of North Carolina at Chapel Hill, Chapel Hill; Xanthon, Inc., Research Triangle Park, both of N.C.

[21] Appl. No.: 08/950,503

[22] Filed: Oct. 14, 1997

Related U.S. Application Data

[63] Continuation-in-part of application No. 08/667,338, Jun. 20, 1996, Pat. No. 5,871,918, which is a continuation-in-part of application No. 08/495,817, Jun. 27, 1995, abandoned.

[51] Int. Cl.⁶ .............................. C12Q 1/68; C12P 19/34
[52] U.S. Cl. .............................................. 435/6; 435/91.2
[58] Field of Search ................................. 435/6, 91.2, 5

[56] References Cited

U.S. PATENT DOCUMENTS

| | | | |
|---|---|---|---|
| 4,545,382 | 10/1985 | Higgins et al. | 128/635 |
| 4,683,195 | 7/1987 | Mullis et al. | 435/6 |
| 4,704,353 | 11/1987 | Humphries et al. | 435/4 |
| 4,800,159 | 1/1989 | Mullis et al. | 435/172.3 |
| 4,840,893 | 6/1989 | Hill et al. | 435/6 |
| 4,883,579 | 11/1989 | Humphries et al. | 204/403 |
| 4,908,307 | 3/1990 | Rodland et al. | 435/6 |
| 4,945,045 | 7/1990 | Forrest et al. | 435/25 |
| 4,963,815 | 10/1990 | Hafeman | 324/715 |
| 4,965,188 | 10/1990 | Mullis et al. | 435/6 |
| 5,066,372 | 11/1991 | Weetall | 204/153.1 |
| 5,108,889 | 4/1992 | Smith | 435/4 |
| 5,112,974 | 5/1992 | Barton | 546/4 |
| 5,143,854 | 9/1992 | Pirrung et al. | 436/518 |
| 5,157,032 | 10/1992 | Barton | 514/185 |
| 5,171,853 | 12/1992 | Thorp et al. | 536/27 |
| 5,175,082 | 12/1992 | Jeffreys | 435/6 |
| 5,194,372 | 3/1993 | Nagai et al. | 435/6 |
| 5,272,056 | 12/1993 | Burrows et al. | 435/6 |
| 5,278,043 | 1/1994 | Bannwarth et al. | 536/23.1 |
| 5,312,527 | 5/1994 | Mikkelsen et al. | 204/153.12 |
| 5,378,628 | 1/1995 | Gratzel et al. | 435/288 |
| 5,405,783 | 4/1995 | Pirrung et al. | 436/518 |
| 5,439,829 | 8/1995 | Anderson et al. | 436/518 |
| 5,532,129 | 7/1996 | Heller | 435/6 |
| 5,565,322 | 10/1996 | Heller | 435/6 |
| 5,605,662 | 2/1997 | Heller et al. | 422/68.1 |
| 5,632,957 | 5/1997 | Heller et al. | 422/68.1 |
| 5,776,672 | 8/1998 | Hashimoto | 435/6 |
| B1 4,683,202 | 11/1990 | Mullis | 435/91 |

FOREIGN PATENT DOCUMENTS

| | | |
|---|---|---|
| 402917 | 12/1990 | European Pat. Off. . |
| 0 478 319 A1 | 9/1991 | European Pat. Off. . |
| 587408 | 3/1994 | European Pat. Off. . |
| 2217007 | 10/1989 | United Kingdom . |
| WO 85/02627 | 6/1985 | WIPO . |
| WO 91/15768 | 10/1991 | WIPO . |
| WO 93/20230 | 10/1993 | WIPO . |
| WO 94/22889 | 10/1994 | WIPO . |
| WO 95/00530 | 1/1995 | WIPO . |
| WO 97/02359 | 1/1997 | WIPO . |

OTHER PUBLICATIONS

R. Khrapko et al.; Hybridization of DNA with oligonucleotides immobilized in gel: convenient method for detection of single base changes, *Mol. Biol. (Moscow)*, 25(3):718–730 (Abstract Only).

(List continued on next page.)

*Primary Examiner*—Eggerton A. Campbell
*Attorney, Agent, or Firm*—Myers Bigel Sibley & Sajovec

[57] ABSTRACT

A polymer-electrode including (a) a substrate having a conductive working surface; and (b) a polymer layer on the conductive working surface. The polymer layer has a plurality of microfluidic reaction openings distributed throughout the layer. An oligonucleotide probe can be attached to the polymer layer and is available to capture target nucleic acid. A soluble mediator can diffuse freely and transfer electrons from the preselected base in the hybridized nucleic acid to the conductive working surface of the substrate. An electronic signal generated from the electron transfer reaction is detected and quantitated.

33 Claims, 5 Drawing Sheets

OTHER PUBLICATIONS

William Bains; The chip of the 90s, *Chemistry in Britain*, 4 pages, Feb.

Carter et al.; Voltammetric Studies of the Interaction of Metal Chelates with DNA. 2. Tris–Chelated Complexes of Cobalt (III) and Iron (II) with 1,10–Phenanthroline and 2,2'–Bipyridine, *J. Am. Chem. Soc.*, 111:8901–8911 (1989).

Chee et al.; Accessing Genetic Information with High–Density DNA Arrays, *Science,* 274:610–614 (1996).

Daube et al.; Typing of Clostridium perfringens by in vitro amplification of toxin genes, *J. of Applied Bacteriology,* 77:650–655 (1994).

Du et al.; [10] Automated FlUorescent DNA Sequencing of Polymerase Chain Reaction Products; *Methods in Enzymology,* 218:104–121 (1993).

Fedorova et al.; Application of Tris(2,2'–bipyridyl)ruthenium(III) for the Investigation of DNA Spatial Structure by a Chemical Modification Method, *J. of Inorganic Biochemistry,* 34:149–155 (1988).

Fodor et al.; Multiplexed biochemical assays with blological chips, *Product Review,* 364:555–556 (1993).

Fodor et al.; Light–Directed, Spatially Addressable Parallel Chemical Synthesis, *Science,* 251:Research Article 767–773 (1991).

Guatelli et al.; Isothermal, in vitro amplification of nucleic acids by a multienzyme reaction modeled after retroviral replication, *Proc. Natl. Acad. Sci USA,* 87:1874–1878 (1990) Biochemistry.

Hall et al.; An Electrochemical Method for Detection of Nucleic Acid Hybridisation, *Biochemistry and Molecular Biology International,* 32(1):21–28 (1994).

Holodniy et al.; Determination of Human Immunodeficiency Virus RNA in Plasma and Cellular Viral DNA Genotypic Zidovudine Resistance and Viral Load during Zidovudine–Didanosine Combination Therapy, *J. of Virology,* 69(6):3510–3516 (1995).

Jenkins et al.; A Sequence–Specific Molecular Light Switch: Tethering of an Oligonucleotide to a Dipyridophenazine Complex of Ruthenium(II), *J. Am. Chem. Soc.,* 114:8736–8738 (1992).

Johnston et al.; Trans–Dioxorhenium(V)–Mediated Electrocatalytic Oxidation of DNA at Indium Tin–Oxide Electrodes: Voltammetric Detection of DNA Clevage in Solution, *Inorg. Chem.,* 33(26):6388–6390 (1994).

Johnston et al.; Electrochemical Measurement of the Solvent Accessibility of Nucleobasis Using Electron Transfer between DNA and Metal Complexes, *J. Am. Chem. Soc.,* 117(35):8933–8938 (1995).

Kwoh et al.; Target amplification systems in nucleic acid–based diagnostic approaches, pp. 14–25 (Oct. 1990).

Kwoh et al.; Transcription–based amplification system and detection of amplified human immunodeficiency virus type 1 with a bead–based sandwich hybridization format, *Proc. Natl. Acad. Sci. USA;* 86:1173–1177 (1989) Biochemistry.

*Genetic Engineering News,* 3 pages, Jun. 1, 1992.

Lishanski et al.; Mutation detection by mismatch binding protein, MutS in amplified DNA: Application to the cystic fibrosis gene, *Proc. Natl. Acad. Sci. USA,* 91:2674–2678 (Mar. 1994).

Lizardi et al.; Exponential Amplification of Recombinant–RNA Hybridization Probes, *Bio/Technology,* 6:1197–1202 (1998).

Lulitanond et al.; Detection of herpes simplex virus 2 Bgl II N fragment in paraffin–embedded cervical tissue sections using nexted polymerase chain reaction, *Molecular and Cellular Probes,* 8:441–447 (1994).

Maeder et al.; Nonlinear Least–Squares Fitting of Multivariate Absorption Data, *Anal. Chem.,* 62:2220–2224 (1990).

L. James Maher III; Inhibition of T7 RNA Polymerase Initiation by Triple–Helical DNA Complexes: A Model for Artificial Gene Repression, *Biochemistry,* 31(33):7587–7594 (1992).

Marchand–Brynaert et al.; Surface Functionalization of Poly(ethylene terephthalate) Film and Membrane by Controlled Wet Chemistry: Chemical Characterization of Carboxylated Surfaces, *J. of Colloid and Interface Sci.,* 173:236–244 (1995).

W. John Martin; *Infectious Diseases, The Polymerase Chain Reaction,* pp. 406–417 (1994).

Meade et al.; Electron Transfer through DNA: Site–Specific Modification of Duplex DNA with Ruthenium Donors and Acceptors, *Angew. Chem. Int. Ed. Engl.,* 34(3):352–354 (1995).

Millan et al.; Sequence–Selective Biosensor for DNA Based on Electroactive Hybridization Indicators, *Anal. Chem.,* 65(17):2317–2323 (1993).

Millan et al.; Voltammetric DNA Biosensor for Cystic Fibrosis Based on a Modified Carbon Paste Electrode, *Anal. Chem.,* 66(18):2943–2948 (1994).

Murphy et al.; Long–Range Photoinduced Electron Transfer Through a DNA Helix, *Science,* 262:1025–1029 (1993).

Murphy et al.; Fast Photoinduced electron transfer through DNA intercalation, *Proc. Natl. Acad. Sci. USA,* 91:5315–5319 (1994).

Neubauer et al.; Prognostic Importance of Mutations in the ras Proto–Oncogenes in De Novo Acute Myeloid Leukemia, *Blood,* 83(6):1603–1611 (1994).

Nielsen et al.; Sequence–Selective Recognition of DNA by Strand Displacement with a Thymine–Substituted Polyamide, *Science,* 254:Reports 1497–1500 (1991).

DNA Sequencing on a Chip, *Analytical Chemistry,* 67(5):201 A–204 A (1995).

Janet Osteryoung; Voltammetry for the Future, *Acc. Che. Res.,* 26(3):77–83 (1993).

Pyle et al.; Mixed–Ligand Complexes of Ruthenium(II): Factors Governing Binding to DNA, *J. Am. Chem. Soc.,* 111(8):3051–3058 (1989).

Ried et al.; Simultaneous visualization of seven different DNA probes by in situ hybridization using combinatorial fluorescence and digital imaging microscopy, *Proc. Natl. Acad. Sci. USA,* 89:1388–1392 (1992).

Rudolph et al.; A Simulator for Cyclic Voltammetric Responses, *Analytical Chemistry,* 66(10):589 A–600 A (1994).

Saleeba et al.; [19] Chemical Cleavage of Mismatch to Detect Mutations, *Methods of Enzymology,* 217:286–295 (1993).

Satyanarayana et al.; Neither Δ– nor Λ–Tris(phenanthroline)ruthenium(II) Binds to DNA by Classical Intercalation; *Biochemistry,* 31(39):9319–9324 (1992).

Schena et al.; Quantitative Monitoring of Gene Expression Patterns with a Complementary DNA Microarray, *Science,* 270:467–470 (1995).

Mellors et al.; Prognosis in HIV–1 Infection Predicted by the Quantity of Virus in Plasma, *Science,* 272:1167–1170 (1996).

Spargo et al.; Chemiluminescent detection of strand displacement amplified DNA from species comprising the *Mycobacterium tuberculosis* complex, *Molecular and Cellular Probes*, 7:395–404 (1993).

Steenken et al.; One–Electron–Reduction Potentials of Pyrimidine Bases, Nucleosides, and Nucleotides in Aqueous Solution. Consequences for DNA Redox Chemistry, *J. Am. Chem. Soc.*, 114(12):4701–4709 (1992).

Strobel et al.; Site–Specific Cleavage of a Yeast Chromosome by Oligonucleotide–Directed Triple–Helix Formation, *Science*, 249:Reports 73–75 (1990).

Strobel et al.; Minor Groove Recognition of the Conserved G•U Pair at the Tetrahymena Ribozyme Reaction Site, *Science*, 267:675–679 (1995).

Titball et al.; Molecular Cloning and Nucleotide Sequence of the Alpha–Toxin (Phospholipase C) of *Clostridium perfringens*, *Infection and Immunity*, 57(2):367–376 (1989).

Tizard et al.; Imaging of DNA sequences with chemiluminescence, *Proc. Natl. Acad. Sci. USA*, 87:4514–4518 (1990).

Tracy et al.; Dynamics of Rigid and Semirigid Rodlike Polymers, *Annu. Rev. Phys. Chem.*, 43:525–557 (1992).

Walker et al.; Strand displacement amplification—an isothermal, in vitro DNA amplification technique, *Nucleic Acids Research*, 20(7):1691–1696 (1992).

Walker et al.; Isothermal in vitro amplification of DNA by a restriction enzyme/DNA polymerase system, *Proc. Natl. Acad. Sci. USA*, 89:392–396 (1992).

Wang et al.; Electrochemical Measurements of Oligonucleotides in the Presence of Chromosomal DNA Using Membrane–Covered Carbon Electrodes, *Anal. Chem.*, 69(19):4056–4059 (1997).

M. J. Waring; Complex Formation between Ethidium Bromide and Nucleic Acids, *J. Mol. Biol.*, 13:269–282 (1965).

Hot Prospect for New Gene Amplified, *Science*, 254:Research News 1292–1293 (1991).

POLYMER-ELECTRODES FOR DETECTING NUCLEIC ACID HYBRIDIZATION AND METHOD OF USE THEREOF

CROSS-REFERENCE TO RELATED APPLICATIONS

The instant application is a continuation-in-part of application Ser. No. 08/667,338, filed Jun. 20, 1996; U.S. Pat. No. 5,871,918, Feb. 16, 1999 which is a continuation-in-part of application Ser. No. 08/495,817, filed Jun. 27, 1995 (now abandoned), the disclosures of which are incorporated herein by reference in their entirety.

BACKGROUND OF THE INVENTION

The present invention relates to electrodes for detecting nucleic acid hybridization and to the method of detecting nucleic acids utilizing such electrodes. The electrodes may also be used for detection of proteins.

The detection of nucleic acid hybridization at solid surfaces has been used for the identification of infectious organisms in clinical specimens (Spargo, C. A. et al., (1993), *Molecular and Cellular Probes* 7, 395–404; Martin, W. J. (1994) Infectious Diseases. In *The Polymerase Chain Reaction* (K. B. Mullis, F. Ferre and R. A. Gibbs, eds.), pp. 406–417. Berkhauser, Boston), the quantitation of mRNA for gene expression analysis (Schena, M., et al., (1995). *Science* 270, 467–470), and the sequencing or resequencing of genomic DNA on high-density "chip" arrays (Chee, M., et al., (1996) Arrays. *Science* 274, 610–613). Presently, these efforts involve the attachment of a fluorescent label to the target nucleic acid, which is then hybridized with a probe-modified surface and detected after washing the unhybridized DNA away from the solid surface. Since detection of photons is required to signal hybridization, analysis of high-density arrays labeled in this manner requires high-resolution fluorescence microscopes. Alternatively, indirect detection of hybridization can be accomplished using sandwich assays where the surface-bound hybrid is subsequently hybridized to an additional signal probe that carries one or more fluorescent labels or enzymes that convert a non-fluorescent substrate to a fluorescent one (Spargo, C. A. et al., (1993), *Molecular and Cellular Probes* 7, 395–404). By attaching multiple enzymes to the signal probes, large signal amplification can be achieved (Holodniy, M. et al., (1995). *J. Virology* 69, 3510–3516); however, the preparation of these multiple enzyme systems is complex.

The patents of Heller (U.S. Pat. Nos. 5,532,129; 5,565,322; 5,605,662; and 5,632,957) disclose the use of an electrode with a permeation layer which is an agarose gel placed on the electrode. A potential is applied to the electrode that brings probe or target DNA to the reaction site on the electrode. Because of the high voltages required, there is a strong possibility of electrooxidation of the probe, target and other components of the solution. The gel protects the system so that excessive levels of target DNA do not accumulate and so that the DNA oxidation is minimized.

Labeled proteins and soluble mediators have been used to detect protein-protein interactions. For example, the patent of Weetall (U.S. Pat. No. 5,066,372) discloses a support layer on a working electrode that is porous to mediator and to which protein can be immobilized. See also U.S. Pat. Nos. 4,945,045 of Hill, 4,545,382 of Higgins, and 5,378,628 of Gratzel. The instant invention differs from these references in that it utilizes guanine as a electron donor to drive the electron transfer reaction rather than utilizing an enzyme oxidation reaction.

The paper of Wang et al. (Wang et al., (1997), *Anal. Chem.* 69, 4056–4059), describes a membrane-covered carbon electrode for analysis of oligonucleotides in the presence of polymeric nucleic acids. The purpose of the membrane is to exclude the polymeric DNA, while small molecules can pass through the membrane for electroanalysis by the carbon electrode. The membrane is not used for attachment of probes and the membrane-covered electrodes do not offer discrimination at the sequence level.

The parent applications, whose entire specifications, drawings, and claims are specifically incorporated herein by reference, disclose, among other inventions, sequencing and methods of qualitatively and quantitatively detecting nucleic acid hybridization.

Such inventions represent a major advance in the art and provide oxidation-reduction complexes which function in a catalytic manner without the addition of an enzyme or fluorescent label, provide for a catalytic current to give the concentration of guanine, or alternate base, in a manner useful for determining the presence or absence of a target, and provide for extremely accurate testing.

Although a major advance, the prior inventions rely on electrodes that are not entirely suitable for measuring the oxidation-reduction reaction. The invention herein provides electrodes coated with a polymer material (a) to which oligonucleotide probes can be covalently attached; (b) in which the soluble mediator can diffuse freely and dock with immobilized DNA; (c) for which no additional electrochemical current is generated at potentials between 0 and +1.3 V (vs a Ag/AgCl reference electrode); and (d) at which the immobilized oligonucleotide probe is available to capture target nucleic acid. In addition, the polymer coating should preferably not adsorb protein or other non-targeted nucleic acid material in biological samples, unlike previously developed electrodes that utilize nylon or nitrocellulose films that have significant affinity for protein and non-complementary nucleic acid. Adsorbed protein, non-targeted nucleic acid, and other biological material contribute to the undesirable background signal and may inhibit proper capture of targeted nucleic acid.

The distinguishing feature of the approach of the invention is that the unlabeled target DNA is differentiated from the synthetic probes by modulation of the electron-transfer reactivity. In the use of the polymer-electrode of the invention, instead of differentiating duplex and single-stranded DNA (as in ethidium bromide fluorescence (Waring, M. J., (1965). *J. Mol. Biol.* 13, 269), we differentiate probe and target. The importance of this difference is that our assay is not dependent on bringing double-stranded DNA to the electrode. Thus, the invention is equally well suited for detection of single- or double-stranded DNA. More importantly, single-stranded RNA, which is of particular interest in identifying unamplified genomic RNA from viruses such as HIV or Hepatitis C, in detecting ribosomal RNA from bacteria, or in quantitating cellular MRNA for gene expression analysis, may also be detected. For the studies described here, the probes are attached to the membrane via the endogenous exocyclic amines of the nucleobases, as has also been done for direct attachment to glassy carbon electrodes (Millan, K. M. et al., (1994), *Anal. Chem.* 66, 2943–2948; Millan, K. M. & Mikkelsen, S. R. (1993). *Anal. Chem.* 65, 2317–2323). Membranes behave similarly with synthetic oligonucleotides to which an alkyl amine linker is appended, which can provide for greater hybridization efficiency and specificity.

Other objects and advantages will be more fully apparent from the following disclosure and appended claims.

SUMMARY OF THE INVENTION

The present invention overcomes the problems of the prior art and provides electrodes which can accurately measure the results of the oxidation-reduction reaction, and provide other critera of covalent oligonucleotide attachment, mediator diffusion, electrochemical inertness, and effective hybridization of target oligonucleotides.

Briefly stated, the present invention is directed to a polymer-electrode useful for the electrochemical detection of a preselected base in a nucleic acid, said polymer-electrode comprising: (a) a substrate having a conductive working surface; and (b) a polymer layer on said conductive working surface, said polymer layer having a plurality of microfluidic reaction openings distributed throughout the layer. An oligonucleotide probe is preferably bound to the polymer layer.

A further aspect of the present invention is a method of detecting and quantitating a nucleic acid utilizing said polymer-electrodes as hereinafter set forth and an apparatus utilizing the polymer-electrodes.

Other objects and features of the inventions will be more fully apparent from the following disclosure and appended claims.

DETAILED DESCRIPTION OF THE INVENTION

Figure 1:
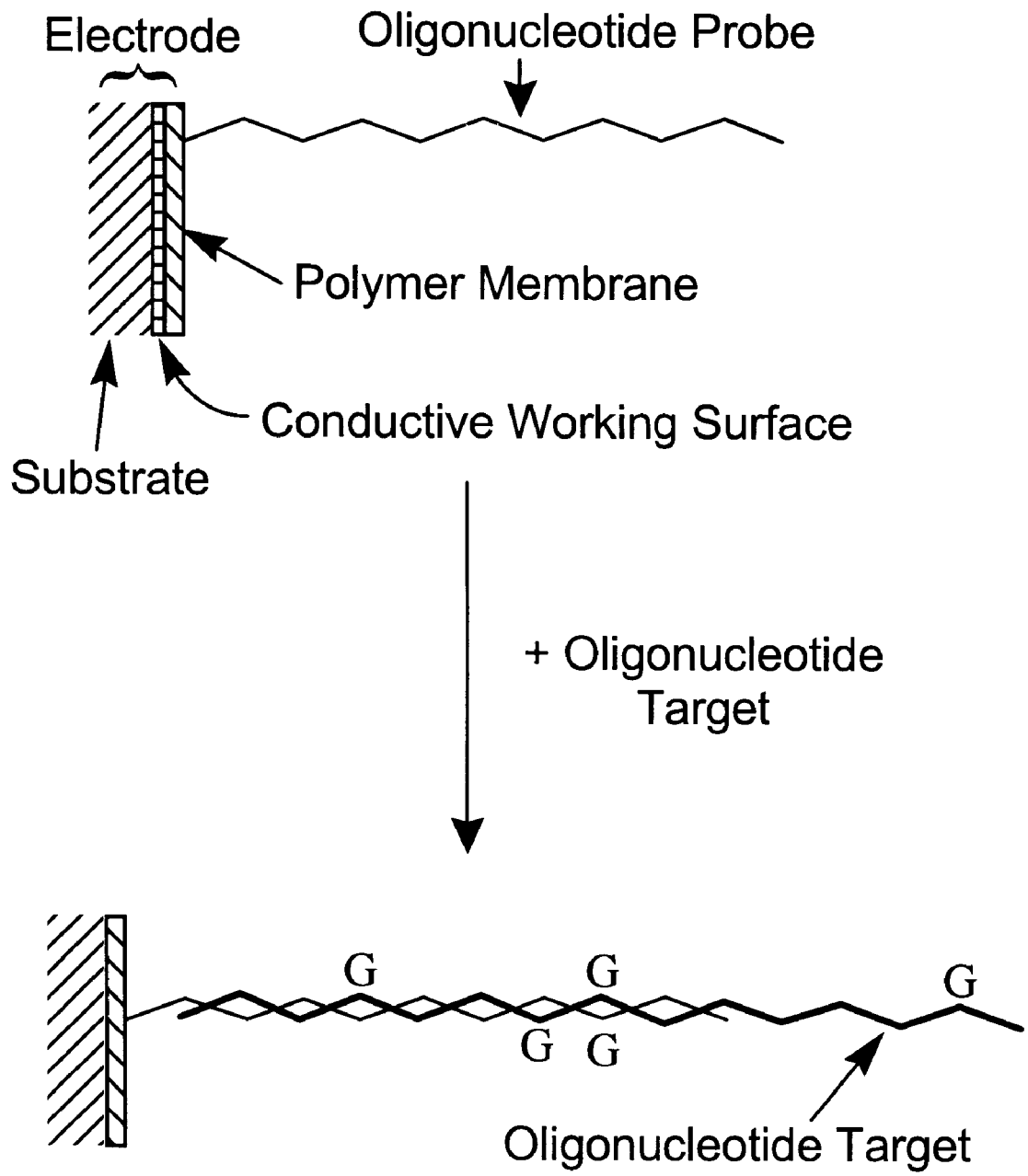
FIG. 1. Method of target strand identification. Oligonucleotide probe containing a sequence complementary to the target oligonucleotide is attached to a polymer membrane in contact with the conductive working surface of the nonconductive substrate. If the target hybridizes with the probe, the target's guanines are detected electrochemically.

In this invention the terms defined below have the same meaning as set forth in the parent applications, with International Application WO 97/01646 corresponding to the parent application having been published on Jan. 16, 1997.

The term "nucleic acid" as used herein refers to any nucleic acid, including both DNA and RNA. Nucleic acids of the present invention are typically polynucleic acids, that is, polymers of individual nucleotides that are covalently joined by 3', 5' phosphodiester bonds.

The term "complementary nucleic acid" as used herein refers to any nucleic acid, including oligonucleotide probes, that specifically binds to another nucleic acid to form a hybridized nucleic acid.

The phrase "determining the presence or absence of" includes both qualitatively determining and quantitatively determining the presence or absence of the detected event (e.g., DNA hybridization, RNA hybridization, detecting target nucleic acid, etc.).

The terms "hybridized DNA" and "hybridized nucleic acid" refer to a single-stranded DNA or nucleic acid which is hybridized to form a double-stranded DNA or nucleic acid, or a double-stranded DNA or nucleic acid which is hybridized to form triple helix DNA or nucleic acid.

While the methods and apparatus of the present invention are sometimes explained with respect to DNA herein, this is for purposes of clarity, and it is to be understood that the methods and apparatus of the instant invention may be applied to other nucleic acids such as RNA.

In addition, the polymer-electrode of the invention has the advantage that it may be used for detection of proteins as well as nucleic acids. As with nucleic acids, no enzyme label is required for use of the invention with proteins, and it is important too use a conductive working surface that is compatible with the mediator used.

The term "polymer-electrode" is used herein to distinguish the electrode of the invention, on which there is a polymer layer, from prior electrodes. This polymer layer can be brought into contact with the substrate at any point during treatment or reacting of the polymer. The completed polymer-electrode of the invention comprises: (a) a substrate having a conductive working surface; and (b) a polymer layer on said conductive working surface.

As is conventional, the electrode used in the invention comprises a substrate with the outer surface functioning as a conductive working surface. The substrate may itself be conductive or it may be nonconductive but have a conductive working surface. The polymer-electrode can have any shape that is conventional in this art, such as an elongate probe having a conductive working surface on the exterior thereof or a flat sheet having the conductive working surface formed on one side thereof. The substrate upon which the polymer layer is placed can be any metal or non-metal material conventionally used, including carbon, such as graphite, glassy carbon, pyrolytic graphite, carbon paste, and carbon fiber; metals, such as platinum, gold, and palladium; doped and undoped oxides, such as indium-doped tin oxide (ITO), tin oxide, titanium oxide, manganese oxide, and lead oxide; and semiconductor materials, such as Si, Ge, ZnO, CdS, $TiO_2$, and GaAs; and the like. It is preferred to use ITO because its properties are relatively well-known, because it is inexpensive, and because it has a high oxidative potential limit in water at neutral pH and a relatively low charging current, and the invention will be further described in connection therewith. Metal substrates cannot have adsorbed thiols or disulfides, because these will oxidize at potentials lower than those needed for guanine oxidation. Some metals, such as gold, oxidize quite easily in aqueous solutions, and their performance can be improved in non-aqueous solutions.

The polymer utilized in the polymer-electrode of the invention must be nonconductive and have openings therethrough. The preferred polymer is polyethylene terephthalate (PET) membranes having pores therein that extend generally perpendicularly from the surface through the film. Such are available commercially under the mark CYCLO-PORE™ from Whatman International (Hillsboro, Oreg.). It is preferred to utilize membranes with a pore size of about 0.4 microns with a density of about $1.5 \times 10^8$ pores/cm$^2$, although a pore size of about 0.1 $\mu$m to 20 $\mu$m is suitable.

In addition to PET it is also possible to use other polymer membranes, such as a polycarbonate, with pores therein, especially those with an essentially neutral surface charge. The polymer membranes can be purchased with the pores therein, or they can be made by the conventional techniques utilized to make porous polymer membranes.

The polymer pores are also referred to herein as "microfluidic reaction openings". When the porous polymer is applied to the conductive working surface of the substrate, the pores, in conjunction with the conductive working surface of the substrate, are believed to form reaction chambers. It is believed that these pores provide a site where the reactants (e.g., $Ru(bpy)_3^{2+}$, DNA or RNA probe and target) are diffusionally retained.

It will be evident that when the polymer layer is placed on the conductive working surface of the substrate, open chambers are formed defined by the continuous side walls of the pores in the polymer layer and the upper surfaces of the substrate against which the polymer layer is placed. Such chambers are referred to herein as "microfluidic reaction chambers." While not completely understood, it is believed that the microfluidic reaction chambers of the instant invention facilitate the catalytic action of the mediators while simultaneously permitting rapid diffusion of the soluble mediator to the immobilized nucleic acid. The microfluidic chambers decrease the operative electrode area by effectively creating an array of micro-scale electrodes underneath each pore, which limits the capacitive current generated by potentiation of the electrode and provides for more planar diffusion. In addition, the local concentration of analyte is greatly increased in the microfluidic pores, which can only be accessed by a single member of the effective microelectrode array. These novel features are combined with the seminal critera of ease of attachment and electrochemical inertness at potentials up to 1.3 V.

The thickness of the polymer layer can vary from 100 Å to 50 microns, or greater. One of skill in the art can optimize pore size and/or polymer layer thickness for a particular target system and the type of biosensor instrument used.

The polymer layer may be placed in contact with the conductive working surface by any suitable means, such as by clamping the polymer layer to the surface, by vacuum, by a liquid interface, or by evaporation of a porous polymer film on the surface. Sufficient contact is required so that electrons may pass through the polymer layer to the conductive surface.

The polymer layer is preferably modified, for example, by oxidation and/or by binding thereto any conventional coupling agent such as a carbodiimide, or to such agents as N-hydroxysuccinimide, glutaraldehyde, His tags, or avidin-biotin binding, in accordance with known techniques.

Polymer-electrodes of the present invention are particularly useful for methods of nucleic acid detection by electrochemical means, as described below, utilizing devices as described in the parent applications and in the International Application noted above, which devices are specifically incorporated herein by reference.

A. Nucleic Acid Amplification Methods

Inasmuch as the processes utilizing the polymer-electrode of the present invention involve contacting the DNA sample to an oligonucleotide probe to produce a hybridized DNA, it may be desirable for certain applications to amplify the DNA prior to contacting with the probe. Amplification of a selected, or target, nucleic acid sequence may be carried out by any suitable means. See generally D. Kwoh and T. Kwoh, (1990). *Biotechnol. Lab.* 8, 14–25. Examples of suitable amplification techniques include, but are not limited to, polymerase chain reaction (including, for RNA amplification, reverse-transcriptase polymerase chain reaction), ligase chain reaction, strand displacement amplification, transcription-based amplification (see D. Kwoh et al., (1989). *Proc. Natl. Acad Sci.* USA 86, 1173–1177), self-sustained sequence replication (or "3SR") (see J. Guatelli et al., (1990). *Proc. Natl. Acad. Sci.* USA 87, 1874–1878), the Q replicase system (see P. Lizardi et al., (1988). *Biotechnology* 6, 1197–1202), nucleic acid sequence-based amplification (or "NASBA") (see R. Lewis, (1992). *Genetic Engineering News* 12 (9), 1), the repair chain reaction (or "RCR") (see R. Lewis, supra), and boomerang DNA amplification (or "BDA") (see R. Lewis, supra). The bases incorporated into the amplification product may be natural or modified bases (modified before or after amplification), and the bases may be selected to optimize subsequent electrochemical detection steps.

Polymerase chain reaction (PCR) may also be carried out in accordance with known techniques, such as those set forth in U.S. Pat. Nos. 4,683,195; 4,683,202; 4,800,159; and 4,965,188 (the disclosures of all U.S. Patent references and publications cited herein are incorporated herein by reference). In general, PCR involves, first, treating a nucleic acid sample (e.g., in the presence of a heat stable DNA polymerase) with one oligonucleotide primer for each strand of the specific sequence to be detected under hybridizing conditions so that an extension product of each primer is synthesized which is complementary to each nucleic acid strand, with the primers sufficiently complementary to each strand of the specific sequence to hybridize therewith so that the extension product synthesized from each primer, when it is separated from its complement, can serve as a template for synthesis of the extension product of the other primer, and then treating the sample under denaturing conditions to separate the primer extension products from their templates if the sequence or sequences to be detected are present. These steps are cyclically repeated until the desired degree of amplification is obtained. Detection of the amplified sequence may be carried out by adding to the reaction product an oligonucleotide probe capable of hybridizing to the reaction product (e.g., an oligonucleotide probe of the parent invention), the probe carrying a detectable label, and then detecting the label in accordance with known techniques. Where the nucleic acid to be amplified is RNA, amplification may be carried out by initial conversion to DNA by reverse transcriptase in accordance with known techniques.

Strand displacement amplification (SDA) may be carried out in accordance with known techniques. See generally G. Walker et al., *Proc. Natl. Acad. Sci.* USA 89, 392–396 (1992); G. Walker et al., *Nucleic Acids Res.* 20, 1691–1696 (1992). For example, SDA may be carried out with a single amplification primer or a pair of amplification primers, with exponential amplification being achieved with the latter. In general, SDA amplification primers comprise, in the 5' to 3' direction, a flanking sequence (the DNA sequence of which is noncritical), a restriction site for the restriction enzyme employed in the reaction, and an oligonucleotide sequence (e.g., an oligonucleotide probe of the present invention) which hybridizes to the target sequence to be amplified and/or detected. The flanking sequence, which serves to facilitate binding of the restriction enzyme to the recognition site and provides a DNA polymerase priming site after the restriction site has been nicked, is preferably about 15 to 20 nucleotides in length; the restriction site is functional in the SDA reaction (i.e., phosphorothioate linkages incorporated into the primer strand do not inhibit subsequent nicking—a condition which may be satisfied through use of a nonpalindromic recognition site); the oligonucleotide probe portion is preferably about 13 to 15 nucleotides in length.

Ligase chain reaction (LCR) is also carried out in accordance with known techniques. See, e.g., R. Weiss, *Science* 254, 1292 (1991). In general, the reaction is carried out with two pairs of oligonucleotide probes: one pair binds to one strand of the sequence to be detected; the other pair binds to the other strand of the sequence to be detected. Each pair together completely overlaps the strand to which it corresponds. The reaction is carried out by, first, denaturing (e.g., separating) the strands of the sequence to be detected, then reacting the strands with the two pairs of oligonucleotide probes in the presence of a heat stable ligase so that each pair of oligonucleotide probes is ligated together, then separating the reaction product, and then cyclically repeating the process until the sequence has been amplified to the desired degree. Detection may then be carried out in like manner as described above with respect to PCR.

Nucleic acid samples produced using these amplification procedures are typically in solution and may be analyzed using the polymer-electrode described herein. The nucleic acid sample is contacted with the oligonucleotide probe by exposing the polymer membrane having the oligonucleotide probe immobilized thereon to the solution containing the nucleic acid sample. Following a wash step, the polymer membrane is contacted to the conductive surface of the substrate, reacted with the mediator and the oxidation-reduction reaction is detected.

B. Oligonucleotide Probes

As noted above, the polymer-electrode of the invention herein and methods of utilizing the polymer-electrode enable detection of hybridized nucleic acid. In this method, a nucleic acid sample is contacted with an oligonucleotide probe to form a hybridized nucleic acid. The oligonucleotide probes which are useful in the methods of the present invention can be any probe comprised of between about 4 or 6 bases up to about 80 or 100 bases or more, more preferably between about 8 and about 30 bases. Oligonucleotide probes may be prepared having any of a wide variety of base sequences according to techniques which are well known in the art. Suitable bases for preparing the oligonucleotide probe may be selected from naturally occurring nucleotide bases such as adenine, cytosine, guanine, uracil, and thymine; and non-naturally occurring or "synthetic" nucleotide bases such as 8-oxo-guanine, 6-mercaptoguanine, 4-acetylcytidine, 5-(carboxyhydroxyethyl)uridine, 2'-O-methylcytidine, 5-carboxymethylamino-methyl-2-thiouridine, 5-carboxymethylaminomethyluridine, dihydrouridine, 2'-O-methylpseudouridine, D-galactosylqueosine, 2'-O-methylguanosine, inosine, 7-deazaguanine, N6-isopentenyladenosine, 1-methyladenosine, 1-methylpseudouridine, 1-methylguanosine, 1-methylinosine, 2,2-dimethylguanosine, 2-methyladenosine, 2-methylguanosine, 3-methylcytidine, 5-methylcytidine, N6-methyladenosine, 7-methylguanosine, 5-methylarninomethyluridine, 5-methoxyaminomethyl-2-thiouridine, D-mannosylqueosine, 5-methoxycarbonylmethyluridine, 5-methoxyuridine, 2-methylthio-N6-isopentenyladenosine, N-((9—D-ribofuranosyl-2-methylthiopurine-6-yl)carbamoyl)threonine, N-((9—D-ribofuranosylpurine-6-yl)N-methyl-carbamoyl)threonine, uridine-5-oxyacetic acid methylester, uridine-5-oxyacetic acid, wybutoxosine, pseudouridine, queosine, 2-thiocytidine, 5-methyl-2-thiouridine, 2-thiouridine, 5-methyluridine, N-((9—D-ribofuranosylpurine-6-yl)carbamoyl)threonine, 2'-O-methyl-5-methyluridine, 2'-O-methylurdine, wybutosine, and 3-(3-amino-3-carboxypropyl)uridine. Any oligonucleotide backbone may be employed, including DNA, RNA (although RNA is less preferred than DNA), modified sugars such as carbocycles, and sugars containing 2' substitutions such as fluoro and methoxy. The oligonucleotides may be oligonucleotides wherein at least one, or all, of the internucleotide bridging phosphate residues are modified phosphates, such as methyl phosphonates, methyl phosphonothioates, phosphoromorpholidates, phosphoropiperazidates and phosphoramidates (for example, every other one of the internucleotide bridging phosphate residues may be modified as described). The oligonucleotide may be a "peptide nucleic acid" such as described in P. Nielsen et al., (1991). *Science* 254, 1497–1500. The only requirement is that the oligonucleotide probe should possess a sequence at least a portion of which is complementary to a known portion of the sequence of the target nucleic acid. It may be desirable in some applications to contact the nucleic acid sample with a number of oligonucleotide probes having different base sequences (e.g., where there are two or more target nucleic acids in the sample, or where a single target nucleic acid is hybridized to two or more probes in a "sandwich" assay).

C. Oxidizing Agents and Oxidation-Reduction Reactions

After hybridization, the hybridized nucleic acid is reacted with a suitable mediator which is capable of oxidizing a preselected base in an oxidation-reduction reaction. The preselected base can be any naturally occurring or synthetic nucleotide base which undergoes oxidation upon reaction with the selected mediator. The preselected base exhibits a unique oxidation rate when paired as compared to when the preselected base is unpaired. The preselected base should exhibit unique oxidation rates when paired with each of the four naturally occurring bases. Generally, bases whose 5'-mononucleotides (e.g., the 5'-deoxyribonucleotide or 5'-ribonucleotide) exhibit rate constants above $10^4 M^{-1}s^{-1}$ can be detected using the catalytic reaction. Examples of suitable preselected bases include but are not limited to guanine, adenine, 8-oxo-guanine, and 8-oxo-adenine, 8-bromo-guanine, xanthine, pseudouridine, 6-mercaptoguanine, 8-mercaptoguanine, 2-thioxanthine, 6-thioxanthine, 6-mercaptopurine, 2-amino-6-carboxymethyl-mercaptopurine, 2-mercaptopurine, 6-methoxypurine, 2-acetylamino-6-hydroxypurine, 6-methylthio-2-hydroxypurine, 2-dimethylamino-6-hydroxypurine, 2-hydroxypurine, 2-aminopurine, 6-amino-2-dimethylallyl-purine, 2-thioadenine, 8-hydroxyadenine, 8-methoxyadenine. Typically, the preselected base is selected from the group consisting of guanine, adenine, 6-mercaptoguanine, 8-oxo-guanine, and 8-oxo-adenine, with guanine being the currently preferred naturally occurring preselected base and 6-mercaptoguanine the currently preferred synthetic preselected base.

The mediator may be any molecule such as a cationic, anionic, non-ionic, or zwitterionic molecule which is reactive with the preselected base at a unique oxidation potential to transfer electrons from the nucleic acid to the electrode. Thus the selection of mediator will be dependent upon the particular preselected base chosen, and will be readily determinable by those skilled in the art. Particularly preferred mediators include transition metal complexes which are capable of metal-nucleic acid electron transfer with the preselected base such that the reduced form of the metal complex is regenerated, completing a catalytic cycle. Examples of suitable transition metal complexes for use in the methods of the present invention include, for example, $Ruthenium^{2+}(2,2'-bipyridine)_3$ ("$Ru(bpy)_3^{2+}$"), $Ruthenium^{2+}(4,4'-dimethyl-2,2'-bipyridine)_3$ ("$Ru(Me_2-bpy)_3^{2+}$"), $Ruthenium^{2+}(5,6-dimethyl-1,10-phenanthroline)_3$ ("$Ru(Me_2-phen)_3^{2+}$"), $Iron^{2+}(2,2'-bipyridine)_3$ ("$Fe(bpy)_3^{2+}$"), $Iron^{2+}(5-chlorophenanthroline)_3$ ("$Fe(5-Cl-phen)_3^{2+}$"), $Osmium^{2+}(5-chlorophenanthroline)_3$ ("$Os(5-Cl-phen)_3^{2+}$"), $dioxorhenium^{1+}phosphine$, and $dioxorhenium^{1+}pyridine$ ("$ReO_2(py)_4^{1+}$"). Some anionic complexes useful as mediators are: $Ru(bpy)((SO_3)_2-bpy)_2^{2-}$ and $Ru(bpy)((CO2)_2-bpy)_2^{2-}$ and some zwitterionic complexes useful as mediators are $Ru(bpy)_2((SO_3)_2-bpy)$ and $Ru(bpy)_2((CO_2)_2-bpy)$ where $(SO_3)_2-bpy^{2-}$ is 4,4'-disulfonato-2,2'-bipyridine and $(CO_2)_2-bpy^{2-}$ is 4,4'-dicarboxy-2,2'-bipyridine. Suitable substituted derivatives of the pyridine, bypyridine and phenanthroline groups may also be employed in complexes with any of the foregoing metals. Suitable substituted derivatives include but are not limited to 4-aminopyridine, 4-dimethylpyridine, 4-acetylpyridine, 4-nitropyridine, 4,4'-diamino-2,2'-bipyridine, 5,5'-diamino-2,2'-bipyridine, 6,6'-diamino-2,2'-bipyridine, 4,4'-diethylenediamine-2,2'-bipyridine, 5,5'-diethylenediamine-2,2'-bipyridine, 6,6'-diethylenediamine-2,2'-bipyridine, 4,4'-dihydroxyl-2,2'-bipyridine, 5,5'-dihydroxyl-2,2'-bipyridine, 6,6'-dihydroxyl-2,2'-bipyridine, 4,4', 4"-triamino-2,2',2"-terpyridine, 4,4',4"-triethylenediamine-2,2',2"-terpyridine, 4,4',4"-trihydroxy-2,2',2"-terpyridine, 4,4',4"-trinitro-2,2',2"-terpyridine, 4,4',4"-triphenyl-2,2',2"-terpyridine, 4,7-diamino-1,10-phenanthroline, 3,8-diamino-1,10-phenanthroline, 4,7-diethylenediamine-1,10-phenanthroline, 3,8-diethylenediamine-1,10-phenanthroline, 4,7-dihydroxyl-1,10-phenanthroline, 3,8-dihydroxyl-1,10-phenanthroline, 4,7-dinitro-1,10-phenanthroline, 3,8-dinitro-1,10-phenanthroline, 4,7-diphenyl-1,10-phenanthroline, 3,8-diphenyl-1,10-phenanthroline, 4,7-disperamine-1,10-phenanthroline, 3,8-disperamine-1,10-phenanthroline, dipyrido[3,2-a:2',2'-c]phenazine, and 6,6'-dichloro-2,2'-bipyridine.

To effect the oxidation-reduction reaction of the mediator with the preselected base, the mediator may be reacted with the hybridized nucleic acid according to any suitable technique. All that is required is that the mediator be reacted with the hybridized nucleic acid sample under conditions sufficient to effect the selective oxidation of the preselected base. The solvent in which the oxidation-reduction reaction takes place may be any suitable solvent for solubilizing DNA, and preferably comprises water. Suitable conditions for permitting the oxidation-reduction reaction to occur will be known to those skilled in the art.

D. Detection of Oxidation-Reduction Reactions

The occurrence of the oxidation-reduction reaction may be detected using a polymer-electrode in accord with the present invention to observe a change in the electronic signal which is indicative of the occurrence of the oxidation-reduction reaction. Typically, a polymer-electrode which is sensitive to the transfer of electrons between the mediator and the hybridized nucleic acid is placed in contact with the solution containing the reacted hybridized nucleic acid and mediator. Generally, a reference electrode and an auxiliary electrode are also placed in contact with the solution in conjunction with the detection electrode (with most of the current passing through the auxiliary electrode). Similarly, suitable reference electrodes will also be known in the art and include, for example, silver/silver chloride electrodes.

The detection of the electronic signal associated with the oxidation-reduction reaction permits the determination of the presence or absence of hybridized nucleic acid. The step of determining the presence or absence of hybridized nucleic acid typically includes (i) measuring the reaction rate of the oxidation-reduction reaction, (ii) comparing the measured reaction rate to the oxidation-reduction reaction rate of the transition metal complex with single-stranded nucleic acid, and then (iii) determining whether or not the measured reaction rate is essentially the same as the oxidation-reduction reaction rate of the transition metal complex with single-stranded nucleic acid. The step of measuring the reaction rate may be carried out by any suitable means. For example, the relative reaction rate may be determined by comparing the current at the same scan rate, probe concentration, target concentration, mediator, buffer, temperature, and/or electrochemical method.

Figure 6:
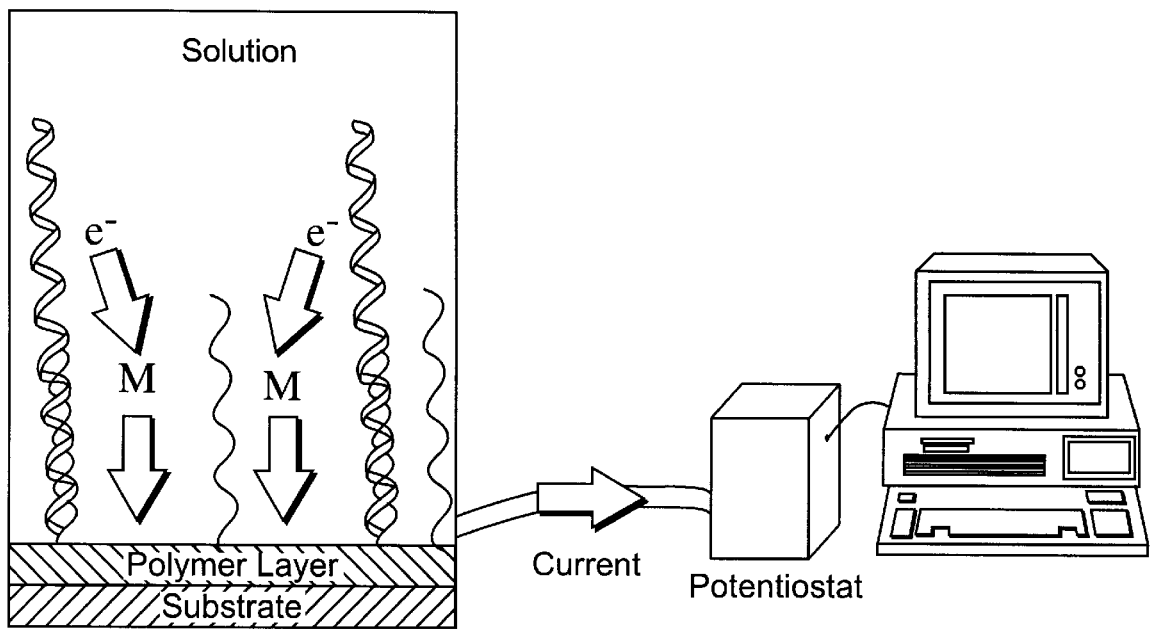
FIG. 6. Biosensor instrument. The electrochemical processes of the biosensor cell are controlled by a potentiostat, an instrument capable of regulating the potential applied to the biosensor cell, and which is also able to measure very small current outputs from the cell. Data from the potentiostat are analyzed and plotted on a conventional computer.

The oxidation-reduction reaction rate may be measured according to suitable means known to those skilled in the art. Typically, the oxidation-reduction reaction rate is measured by measuring the electronic signal associated with the occurrence of the oxidation-reduction reaction. For example, the electronic signal associated with the oxidation-reduction reaction may be measured by providing a suitable apparatus in electronic communication with the polymer-electrode disclosed herein. A suitable apparatus is a potentiostat capable of measuring the electronic signal which is generated so as to provide a measurement of the oxidation-reduction reaction rate of the reaction between the hybridized nucleic acid and the mediator. The electronic output may be characteristic of any electrochemical method, including cyclic voltammetry, normal pulse voltammetry, chronoamperometry, and square-wave voltammetry, with cyclic voltammetry being the currently preferred form. A computer as is known in the art may be used for controlling the use of the polymer-electrode and for recording results of such use. An example of such an apparatus with which the polymer-electrode of the invention may be used is shown in FIG. 6.

The measured reaction rate may then be compared to the known oxidation-reduction reaction rate of the transition metal complex with a single-stranded DNA. The tunneling distance between the mediator and the preselected base in either the hybridized or single-stranded DNA affects the oxidation-reduction reaction rate of the reaction between the mediator and the preselected base. Accordingly, hybridized DNA exhibits a different oxidation-reduction reaction rate than single-stranded DNA. The presence or absence of hybridized DNA at the preselected base can be determined by determining whether or not the measured oxidation-reduction reaction rate is the same as the oxidation-reduction reaction rate of the mediator and the preselected base in single-stranded DNA. Furthermore, the tunneling distance between the mediator and the preselected base will differ according to the bond distance between the preselected base and its pair, such that each possible base pairing may be distinguished from the others. The bond distance between the preselected base and its base pair is dependent upon the base which is paired with the preselected base. For example, the oxidation-reduction reaction rate for the oxidation of guanine paired with adenine differs from the oxidation-reduction reaction rate for the oxidation of guanine paired with cytosine, which in turn is different from the oxidation-reduction reaction rate for the oxidation of guanine paired with guanine, which is also different from the oxidation-reduction reaction rate for the oxidation of guanine paired with thymine. More specifically, the oxidation-reduction reaction rates for the oxidation of guanine follow the trend wherein single strand guanine is greater than guanine paired with adenine, which is greater than guanine paired with guanine, which is greater than guanine paired with thymine, which is greater than guanine paired with cytosine. Accordingly, the polymer-electrode and methods of the present invention are useful for detecting single-base pair mismatches at the preselected base or at the base pair adjacent to the preselected base.

Advantageously, the distinction between the oxidation-reduction reaction rates of the oxidation of the preselected base when paired with each of the various naturally occurring bases also permits the identification of the base paired with the preselected base. The base paired with the preselected base may be identified by (i) measuring the reaction rate of the detected oxidation-reduction reaction, (ii) comparing the measured reaction rate to each of the four different known oxidation-reduction reaction rates of the mediator with a DNA having adenine, cytosine, guanine, or thymine bound to the preselected base, and (iii) determining which of the known oxidation-reduction reaction rates is essentially the same as the measured reaction rate. The reaction rate may be measured according to techniques described above. Similarly, the reaction rates of each of the four different oxidation-reduction reactions of the mediator with a DNA having adenine, cytosine, guanine or thymine bound to the preselected base may be measured according to the same techniques such that these reaction rates are known. The measured reaction rate of the oxidation-reduction reaction of the mediator with the hybridized DNA may then be compared to the known oxidation-reduction reaction rates of the mediator with a DNA having adenine, cytosine, guanine or thymine bound to the preselected base. For example, the base paired with the preselected base is determined from comparison of the measured oxidation-reduction reaction rate with predicted reaction rates for each type of base pairing.

E. Detection of Preselected Base on Target Nucleic Acid

In the methods described in co-pending Ser. No. 08/667,337, metal complexes are used to obtain an electrochemical current from single- and double-stranded nucleic acids. Preselected bases such as guanine give an electrochemical signal, and this signal is much weaker for double-stranded DNA. Such methods advantageously exhibit high structural sensitivity, and can resolve a single base mismatch. Such methods are therefore particularly advantageous for the sequencing of DNA. However, two drawbacks of such methods are that: (a) there is a negative signal on going from the probe strand to the hybrid, and (b) the number of preselected bases is limited which limits the signal. The following techniques provide solutions to these problems. In addition, the following techniques are particularly useful for diagnostic assays, and are particularly useful for the quantitative detection of nucleic acids.

In view of the foregoing, also disclosed herein and in Ser. No. 08/667,337, is a method of detecting the presence or absence of a target nucleic acid in a test sample suspected of containing the same, wherein the target nucleic acid contains at least one preselected base. In this method, the preselected base is located on the target nucleic acid, rather than on the oligonucleotide probe.

The method may be carried out on a test sample containing the target nucleic acid. Any test sample suspected of containing the target nucleic acid may be used, including, but not limited to, tissue samples such as biopsy samples and biological fluids such as blood, sputum, urine and semen samples, bacterial cultures, soil samples, food samples, etc. The target nucleic acid may be of any origin, including animal, plant or microbiological (e.g., viral, prokaryotic, and eukaryotic organisms, including bacterial, protozoal, and fungal, etc.) depending on the particular purpose of the test. Examples include surgical specimens, specimens used for medical diagnostics, specimens used for genetic testing, environmental specimens, food specimens, dental specimens and veterinary specimens. The sample may be processed or purified prior to carrying out the instant method in accordance with techniques known or apparent to those skilled in the art; and nucleic acids therein may be digested, fragmented, and/or amplified (see above) prior to carrying out the instant method, if so desired.

As schematically illustrated in FIG. 1, the method of this invention, which may be used for detection of a preselected base on a target nucleic acid, comprises (a) contacting the test sample to an oligonucleotide probe that specifically binds to the target nucleic acid to form a hybridized nucleic acid; (b) contacting the hybridized nucleic acid to a transition metal complex that oxidizes the preselected base in an oxidation-reduction reaction; (c) detecting the presence or absence of the oxidation-reduction reaction associated with the hybridized nucleic acid; and (d) determining the presence or absence of the target nucleic acid in the test sample from the detected oxidation-reduction reaction at the preselected base. As illustrated in FIG. 1, the oligonucleotide probe may be immobilized on a solid support (the polymer layer) to facilitate separating the test sample from the hybridized nucleic acid, with the separating step occurring prior to the detecting step (e.g., between steps (a) and (b) or betweens steps (b) and (c)). Alternatively, the oligonucleotide probe may be provided free in solution, and other means provided to separate the hybridized nucleic acid from the sample (e.g., by a mediator nucleic acid that binds to the oligonucleotide probe, or by a biotin-avidin binding interaction, where biotin is bound to the oligonucleotide probe and avidin is immobilized on a solid support). The oxidation-reduction reaction, and any step up to the detection step may be done on the polymer layer before or after the polymer layer is brought into contact with the conductive working surface of the substrate.

Preferably, the target nucleic acid contains at least ten more of the preselected base than does the oligonucleotide probe, or more preferably at least 50 or 100 more of the preselected base than does the oligonucleotide probe. A larger current enhancement is advantageously obtained when the target nucleic acid contains many more of the preselected base than does the oligonucleotide probe.

Optionally, but preferably, the oligonucleotide probe is free of the preselected base, or is at least essentially free of the preselected base (i.e., contains sufficiently less of the preselected base so that signal from probe does not interfere with or is not mistaken as a signal from the target nucleic acid). Where a sequence of naturally occurring bases that will conveniently hybridize to the target nucleic acid is not available, the strategy of employing alternate bases that are redox inactive (discussed below) may be employed.

The target nucleic acid is preferably longer than the oligonucleotide probe, and at least one of the preselected bases is "overhanging", i.e., as illustrated in FIG. 1, not hybridized to the oligonucleotide probe in the hybridized nucleic acid. Preferably, at least 10, 50, or 100 of the preselected bases are "overhanging" bases, thereby providing substantial amplification of the electrochemical signal detected.

For example, an oligonucleotide probe that does not contain any guanine residues (e.g., only A, T, and C) may be chosen. The cyclic voltammogram of Ru $(bpy)_3^{2+}$ in the presence of this strand is very similar to that without the oligomer. This probe is then hybridized to a target strand that contains guanines in either the overlapping base-paired regions and/or in overhanging regions if the target nucleic acid is longer than the oligonucleotide probe. Because multiple guanines are detected, the signal is amplified relative to the number of hybrids formed. In a case where a genomic DNA or RNA is the target strand, large numbers of overhanging guanines are encountered, which would give tremendous signal amplification.

For example, in one preferred embodiment, the assay for the preselected base on the target strand involves immobilization of the (preferably redox-silent) probe strand on the polymer layer oriented close to the electrode surface, which provides a low background signal when scanned in the presence of the mediator. The polymer layer is then contacted with a solution of the target strand, which contains the preselected base. If hybridization occurs, the target strand will now be in close proximity to the electrode, and a current enhancement will be detected in presence of mediator.

Quantitating Nucleic Acids. The above-described method is particularly well suited to the quantitative detection of nucleic acids. In the case described in this section, the rate constant for oxidation of the hybrid by the mediator (e.g., $Ru(bpy)_3^{2+}$) can be determined from the cyclic voltammogram (or other electronic signal) by digital simulation. Under most conditions, this reaction will obey second-order kinetics, so the rate=$k[Ru(bpy)_3^{2+}][DNA]$ where k is the rate constant that is specific for the particular probe-target hybrid, $[Ru(bpy)_3^{2+}]$ is the concentration of the mediator, and [DNA] is the concentration of the hybrid (which could be a DNA-RNA hybrid). If k and $[Ru(bpy)_3^{2+}]$ are known, then the quantity of the hybrid can be determined. In practice, a calibration curve for current enhancements obtained with different quantities of standard solutions containing target DNA or RNA is constructed and the current enhancement used to obtain the quantity of hybrid directly. This quantity is then related directly to the quantity of target material (e.g., infectious organism in a clinical sample). See, e.g., M. Holodniy et al., (1995), *J. Virol.* 69, 3510–3516; J. Mellors et al., (1996). *Science* 272, 1167–1170.

F. Alternate Bases That Are Redox Inactive

Figure 4:
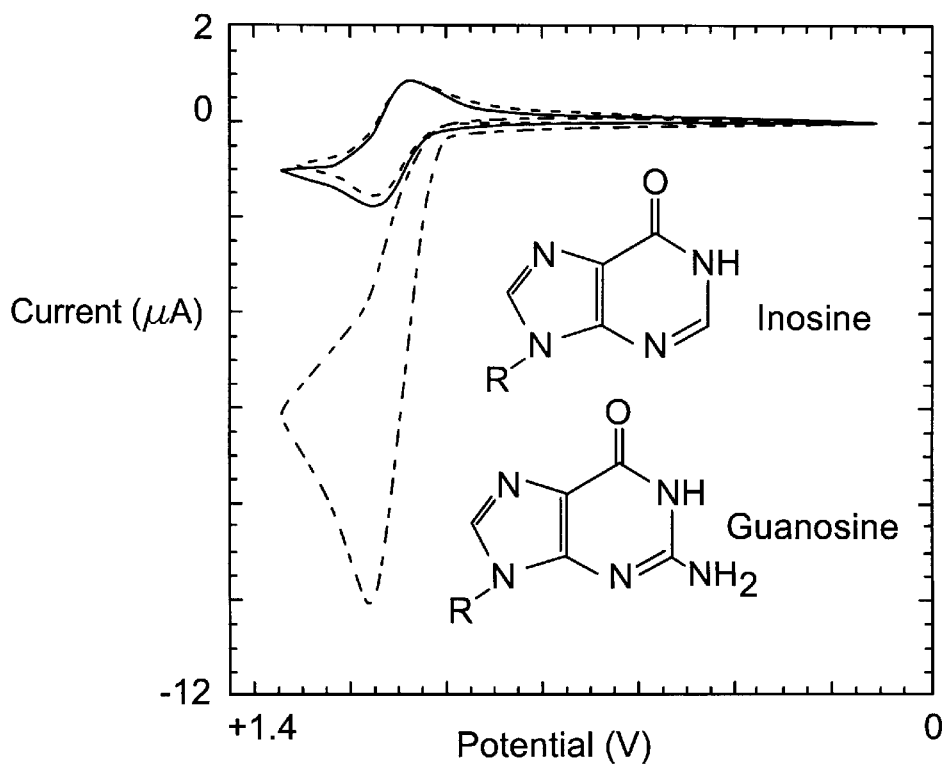
FIG. 4. Cyclic voltammograms of $Ru(bpy)_3^{2+}$(25 $\mu$M) (dotted), with inosine 5'-monophosphate (0.3 mM)(solid), and with guanosine 5'-monophosphate (0.3 mM)(dashed). Scan rate: 25 mV/s.

An alternate base may be used that would substitute for guanine (i.e., a base that, like guanine, has a greater binding affinity for cytosine than do other bases in a nucleic acid duplex) in the probe strand but would not be oxidized by the mediator under the applicable reaction conditions. When the preselected base in the target nucleic acid is guanine and the target nucleic acid also contains cytosine (which ordinarily bonds with guanine in the probe), then the probe contains an alternate base that bonds to cytosine in the hybridized nucleic acid. The alternate base may be selected from the group consisting of inosine and 7-deazaguanine. As shown in FIG. 4, inosine is three orders of magnitude less reactive than guanine. The reacting step typically comprises reacting the transition metal complex with the nucleic acid under conditions sufficient to effect the selective oxidation of the preselected base without oxidizing the alternate base.

Thus, a method of detecting a target nucleic acid, where the target nucleic acid contains at least one preselected base and the probe or capture nucleic acid contains alternate redox inactive bases comprises: (a) contacting the target nucleic acid to a complementary nucleic acid that specifically binds to the target nucleic acid to form a hybridized nucleic acid; (b) reacting the hybridized nucleic acid with a transition metal complex capable of oxidizing the preselected base in an oxidation-reduction reaction; (c) detecting the oxidation-reduction reaction; and (d) determining the presence or absence of the nucleic acid from the detected oxidation-reduction reaction at the preselected base.

G. Representation of the Preferred Polymer-Electrode

Figure 2:
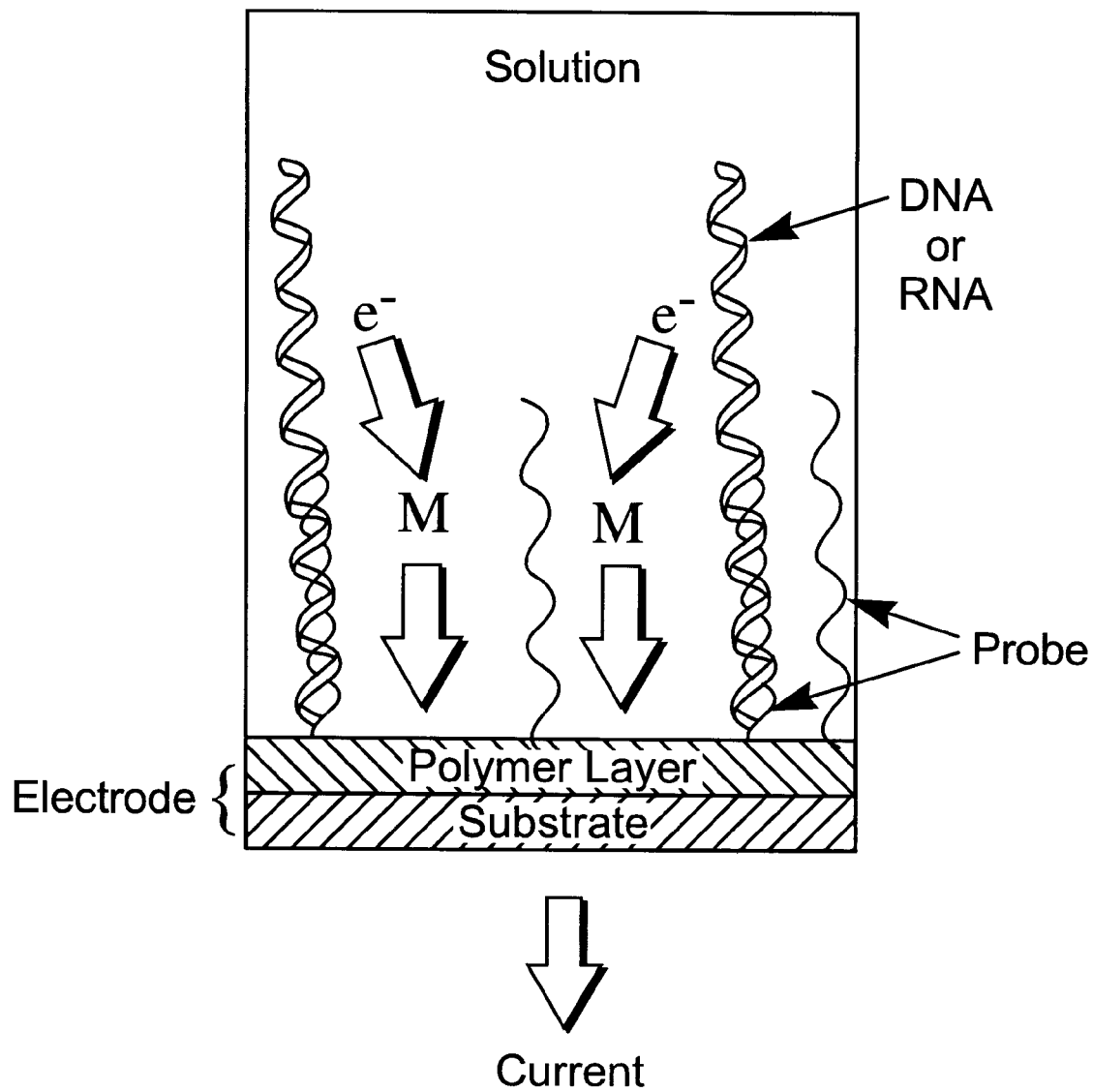
FIG. 2. Scheme showing the preferred biosensor design. The nucleic acid is immobilized to a polymer layer composed of a porous polyethylene terephthalate (PET) membrane. Electron transfer occurs from guanosine-containing target nucleic acid (heavy strands) to the mediator (M, $Ru(bpy)_3^{2+}$) through the polymer membrane to the conductive surface of the substrate, producing a current. Minimal electron transfer occurs from the inosine-substituted probe nucleic acid (light strands).

A schematic representation of a biosensor cell to detect nucleic acid in solution is shown in FIG. 2. The cell consists of a chamber with the polymer-electrode at one end. The oligonucleotide probe attached to the polymer layer is hybridized with the complementary target nucleic acid and then the polymer layer is contacted to the conductive working surface of the substrate. Alternatively, the sample solution containing the target nucleic acid may be added directly to the chamber with the polymer-electrode in place and hybridization carried out inside the chamber. After hybridization, the mediator solution is added and a potential applied. Electrons from guanine are transferred to the conductive surface by the mediator producing a detectable current.

The invention will be further described in connection with the following examples which are set forth for purposes of illustration only.

EXAMPLES

Introduction to Examples. The detection of nucleic acids by hybridization is of prime importance in diagnosing infectious diseases, quantitating gene expression, and sequencing genomic DNA on oligonucleotide arrays. Most methods for detecting and quantitating hybridized nucleic acid rely on the attachment of a fluorescent, chemiluminescent, or radioactive label to the target strand. Here we describe an alternative method based on an electron-transfer reaction between guanine in native DNA and a transition-metal complex that can be electrochemically activated. The presence of DNA is indicated by catalytic current observed in the cyclic voltammogram of the transition-metal complex. Polymer-electrodes are prepared by bringing a tin-doped indium oxide electrode into contact with an oxidized polyethylene terephthalate membrane to which probe strands have been covalently attached. These probe strands are specially engineered by replacement of guanine with inosine. Hybridized DNA target contains guanine and is therefore more redox-active than the probe strand. The sensor electrodes are tested in model reactions for the detection of a synthetic 21-mer based on the ras oncogene sequence shown in Table 1. The same design is applied to the detection of PCR products from the amplification of genomic RNA from Human immunodeficiency virus (HIV) and genomic DNA from Herpes simplex virus type II and *Clostridium perfringens*.

EXAMPLE 1. Reagents and DNA.

The inorganic reagents used in the following examples are of analytical grade or higher. HCl and $H_2SO_4$ are obtained from Fisher Scientific (Pittsburgh, Pa.). Water-soluble carbodiimide (WSC, 1-(3-dimethylaminopropyl)-3-ethylcarbodiimide hydrochloride) and potassium permanganate are obtained from Aldrich (Milwaukee, Wis.). $Na_2HPO_4$, $NaH_2PO_4$, and NaCl are obtained from Mallinckrodt (Phillipsburg, N.J.). Water is obtained from a Milli-Q Plus purification system (Millipore, Bedford, Mass.). Synthetic oligonucleotides (Table 1) are synthesized by the UNC Department of Pathology and purified using Amicon micron 3 concentrators with a cutoff of 3000 molecular weight. Genomic DNA from Herpes simplex II virus (HSV) and *Clostridium perfringens* bacterial DNA is obtained from Sigma Chemical (St. Louis, Mo.). The reverse transcriptase-PCR (RT-PCR) reaction of a 3.2 kb fragment from the gp160 gene of HIV is performed using the primers in Table 1.

TABLE 1

Oligomer Sequences used as probes and primers

| | Oligomer Sequences |
|---|---|
| 21-mer ras probe | 5'-ITACTCTTCTTITCCAICTIT |
| 21-mer complement | 5'-ACAGCTGGACAAGAAGAGTAC |
| 21-mer control | 5'-ACATCGAGCTTAAGGTGTCGC |
| HIV primers | 5'-CCGGAATTCTGCAACAACTGCTG |
| | 5'-CCGCTCGAGATGCTGGTCCCA |
| HIV probe | 5'-AAACAAATTCCACAAACTTGC |
| HSV primers[a] | 5'-CGACATCAACCACCTTCGCT |
| | 5'-ATGTAGCACGAGGCTGTCGT |
| HSV probe[a] | 5'-ICCCICACCATCCAACCACCC |
| C perfringens primers[b] | 5'-TGCTAATGTTACTGCCGTTGATAG |
| | 5'-ATAATCCCAATCATCCCAACTATG |
| C perfringens probe[b] | 5'-CAAAAIAATATICAAIATITT |

[a](Lulitanond, V. et al., (1994). Mol. Cell Probes 8, 441–447)
[b](Daube, G. et al., (1994). J. Appl. Bacteriology 77, 650–655)

EXAMPLE 2. Preparation and Activation of the Carboxylated Polymer Membranes.

Polyethylene terephthalate track-etched membranes (CYCLOPORE™) with a pore size of 0.4 μm and a diameter of 25 mm are obtained from Whatman International (Hillsboro, Oreg.). The CYCLOPORE™ membranes preferably used in this invention are carboxylated to allow attachment of the probes. Four circular sample disks, approximately 8 mm in diameter are cut from each 25 mm membrane. The carboxylated polymer membranes are prepared following an adaptation of the procedure published in *J. Coll. Interface Sci.*, 173, 236–244 by Marchand-Brynaert, J. et al. The polymer disks are treated with a solution of $KMnO_4$ in 1.2 N $H_2SO_4$ (2.5 g/50mL) for approximately 18 hours at room temperature. The polymer disks are then washed with 6N HCl (2×30 minutes, 25° C.) to remove the brown manganese oxide followed by water rinses (3×30 minutes, 25° C.). The carboxylation of the polymer film is confirmed by X-ray photoelectron spectroscopy (XPS) analysis with an increase in the O/C ratio from 0.363 to 0.398 following treatment. These results and those obtained at each step in the functionalization compare favorably to those obtained by others in protein immobilization (Marchand-Brynaert, J. et al., (1995). *J. Coll. Interface Sci.* 173, 236–244).

EXAMPLE 3. Dry Attachment.

The activation of the surface carboxylate moieties is performed by application of 30 μL of freshly prepared 10 mM water-soluble carbodiimide (WSC) in 20 mM sodium phosophate buffer (pH 7.0) to each side of the polymer disk. After each application, the polymer is allowed to dry. The polymer disks are then rinsed twice with 20 mM sodium phosphate buffer and once with water. The DNA probes are coupled to the activated polymer membranes by application of 0.75 nmol of probe in 10 μL water to each side of the membrane to give a surface density of approximately 5 nmol/cm². The polymer is allowed to dry after each application. The polymer disks are then rinsed twice with 20 mM sodium phosphate buffer and once with water. The polymer disks with the probe attached are now ready for hybridization.

EXAMPLE 4. Wet Attachment.

In this alternative to the dry attachment method set forth above, carboxylated CYCLOPORE™ membranes are activated toward DNA attachment by exposing them to a solution of 200 mM water-soluble carbodiimide (WSC) and 50 mM N-hydroxysuccinimide (NHS) in water for 20 minutes. The membranes are removed and washed in water by shaking for one minute. The activated membranes are then exposed to a solution of 0.1 mM DNA in an aqueous buffer at room temperature for 20 minutes to one hour. The membranes are removed and washed sequentially by shaking in water once, then in the aqueous buffer once, and then in water twice for approximately 10 minutes each cycle. The carboxylated membranes with the DNA probes attached are now ready for hybridization.

Either the dry attachment technique or the wet attachment technique may be used prior to hybridization to attach the probe to the membrane. The dry method has a higher background associated with it and is more time-consuming. The dry method can also be more variable, but can at times show very high levels of probe attachment. The wet method is faster and more consistent but the amount of probe attached is sometimes lower than that seen with the dry method. There are thus advantages and disadvantages of each method as compared with the other.

EXAMPLE 5. Hybridization for Direct Detection of Synthetic 21-mer Hybridization.

Polymer films to which an inosine-substituted 21-mer probe (Table 1) is coupled are placed into 200 μL of a hybridization buffer of 50 mM sodium phosphate and 800 mM NaCl with 1 nmol of the complementary or control 21-mer DNA. The hybridization buffer and polymer film are heated for one hour at 50° C. and slowly cooled to room temperature. The polymer membrane is removed from the liquid and washed twice in 20 mM sodium phosphate buffer and once with water prior to electrochemical analysis.

EXAMPLE 6. Amplification of Biological Samples.

All DNA samples are amplified using the polymerase chain reaction method as described elsewhere (Daube, G. et al., (1994). *J. Appl. Bacteriology* 77, 650–655; Lulitanond, V. et al., (1994). *Mol. Cell Probes* 8, 441–447). The reaction tubes contained 80 µL of a solution of approximately 1 pmol (in nucleotide) sample DNA, 10 mM Tris-HCl, pH 8.4,50 mM KCl, 200 µM dNTP, and either 2.5 mM $MgCl_2$ (HIV & HSV) or 3 mM $MgCl_2$ (*Clostridium perfringens*). The primer sequences (Table 1) are for a 247 bp fragment of the a-toxin gene of *C. perfringens* (Daube, G. et al., (1994). *J. Appl. Bacteriology* 77, 650–655; Titball, R. W. et al., (1989). *Infect. Immun.* 57, 367–376), for a 561 bp amplicon from the Bgl II N fragment from HSV (Lulitanond, V. et al., (1994). *Mol. Cell Probes* 8, 441–447), or for a 3.2 kb amplicon from the gp160 gene of HIV. The primers are added to a final concentration of 4 $\mu$M, and 1–2 units *Taq* polymerase (Perkin-Elmer, Norfolk, Conn., USA) are added to the mixture using the hot-start method of preheating the reaction tube to 94° C. for 5 min. The mixtures are subjected to 45 cycles at 94° C. for 1 min, 55° C. for 1 min, and 70° C. for 2 min with an automatic thermal cycler (Perkin-Elmer Model 2400). Each set of amplification reactions contains both positive and negative controls, and each mixture is analyzed by agarose gel electrophoresis to verify that amplicons of the appropriate size are produced and that the positive and negative controls behave appropriately.

EXAMPLE 7. Hybridization of PCR products

To hybridize the PCR products, polymer films modified with the appropriate inosine-substituted probe (Table 1) are placed into the hybridization buffer with a 60 $\mu$L aliquot of the unpurified HIV, HSV, or *C. perfringens* PCR reaction and heated for 10 minutes at 95° C. in a total volume of 200 $\mu$L. The polymer films are allowed to hybridize in the buffer overnight. As a control, the non-complementary inosine-substituted ras 21-mer probe is coupled to a polymer membrane and exposed similarly to the PCR reactions. The polymer membrane is removed from the liquid and washed twice in 20 mM sodium phosphate buffer and once with water prior to contact with the conductive surface and subsequent electrochemical analysis.

EXAMPLE 8. Electrochemical analysis.

Cyclic voltammograms are collected using a PAR 273A potentiostat/galvanostat with a single compartment biosensor cell equipped with a Pt-wire counter electrode and an Ag/AgCl reference electrode. In a typical experiment, prior to analysis the polymer membrane is placed on top of an indium tin oxide (ITO) conductive working surface (area 0.32 $cm^2$) at the base of the biosensor cell and held in place with an o-ring. 200 $\mu$L of 100 $\mu$M $Ru(bpy)_3^{2+}$in 50 mM sodium phosphate buffer (pH 7.0) is placed into the cell chamber and allowed to equilibrate with the polymer-electrode for 20 minutes. The polymer film covers all of the exposed ITO conductive surface so that the $Ru(bpy)_3^{2+}$is forced to diffuse through the film to access the conductive surface. The controlled porosity of the polymer membrane provides microfluidic reaction chambers for adequate cycling action of the $Ru(bpy)_3^{2+}$. Cyclic voltammograms from 0.0 to 1.3 V are taken at a scan rate of 25 mV/sec. A freshly cleaned ITO substrate is used for each sample, and a background scan of buffer alone is collected and subtracted from subsequent scans. The quantities of charge (in microcoulombs, $\mu$C) shown in the bar graphs in FIGS. 3 and 5 are obtained by integrating the cyclic voltammograms between 900 mV and 1300 mV and subtracting the charge for the probe-modified polymer membranes from the charge for the hybridization and control reactions.

EXAMPLE 9. Preparation of sensor electrodes.

As shown by Marchand-Brynaert et al. (Marchand-Brynaert, J. et al., (1995). *J. Coll. Interface Sci.* 173, 236–244), oxidation of the alcohol chain ends of the track-etched microporous polymer membranes with $KMnO_4$ results in the formation of carboxylic acid functionalities that can be linked to proteins and amino acids via carbodiimide-catalyzed reaction of amine groups to form amide linkages. The invention herein shows that single-stranded DNA probes can also be coupled to the carboxylic acid groups of the polymer membrane via the exocyclic amines of the nucleobases. The DNA attachment is followed by XPS, which shows changes at each step similar to those observed for amino acid functionalization (Marchand-Brynaert, J. et al., (1995). *J. Coll. Interface Sci.* 173, 236–244) except that peaks due to ionization of phosphorus and an increase in the peaks due to ionization of nitrogen are apparent following DNA coupling. Similarly, cyclic voltammograms of the membranes exposed to probe with no WSC resemble the voltammograms of membranes with no exposure to DNA, demonstrating a low degree of nonspecific DNA binding. When attached to ITO substrates, the DNA covalently attached to the polymer layer is accessible to $Ru(bpy)_3$ $^{2+}$, which can shuttle electrons from guanine to the conductive working surface. If inosine-substituted oligonucleotides are used as immobilized probes, then relatively small catalytic currents are observed. If the immobilized inosine-substituted probes are then hybridized to strands containing guanine, large catalytic currents are found due to the shuttling of electrons from the hybridized DNA to the conductive surface by the $Ru(bpy)_3^{2+}$mediator.

EXAMPLE 10. Direct detection of DNA.

The sensor design is first tested using synthetic 21-mer oligonucleotides patterned on the ras oncogene sequence (Neubaeur, A., et al., (1994) *Blood* 83, 103–1611)(Table 1). No current above background is observed for the probe-modified polymer-electrodes in the absence of $Ru(bpy)_3^{2+}$ before or after hybridization, indicating that direct electron transfer from the immobilized DNA to the conductive surface has not occurred. However, measurable current due to DNA is always observed in cyclic voltammograms of $Ru(bpy),^{2+}$in the presence of polymer membranes modified with the inosine-subsituted 21-mer probe and after hybridization. As shown in FIG. 3A, a significant increase in current is observed for the polymer membrane undergoing hybridization to the complementary 21-mer DNA (solid) when compared to the polymer membrane containing only the inosine-substituted probe (dotted) or after exposure to the 21-mer control sequence (dashed). This current increase suggests that the hybridization event is successful and that electron transfer from the guanines of the hybridized strand to $Ru(bpy)_3^{3+}$and hence to the conductive surface is responsible for the increase in oxidation current. In contrast, very little current increase is observed for the polymer membrane exposed to the 21 -mer control DNA. The inset in FIG. 3 shows the charge acquired for the hybridization and control reactions after subtraction of the charge acquired at the probe-modified polymer-electrode and indicates sufficient signal-to-noise ratio for detection of the target sequence.

EXAMPLE 11. Results of Synthetic 21-mer Hybridization.

Figure 3A:
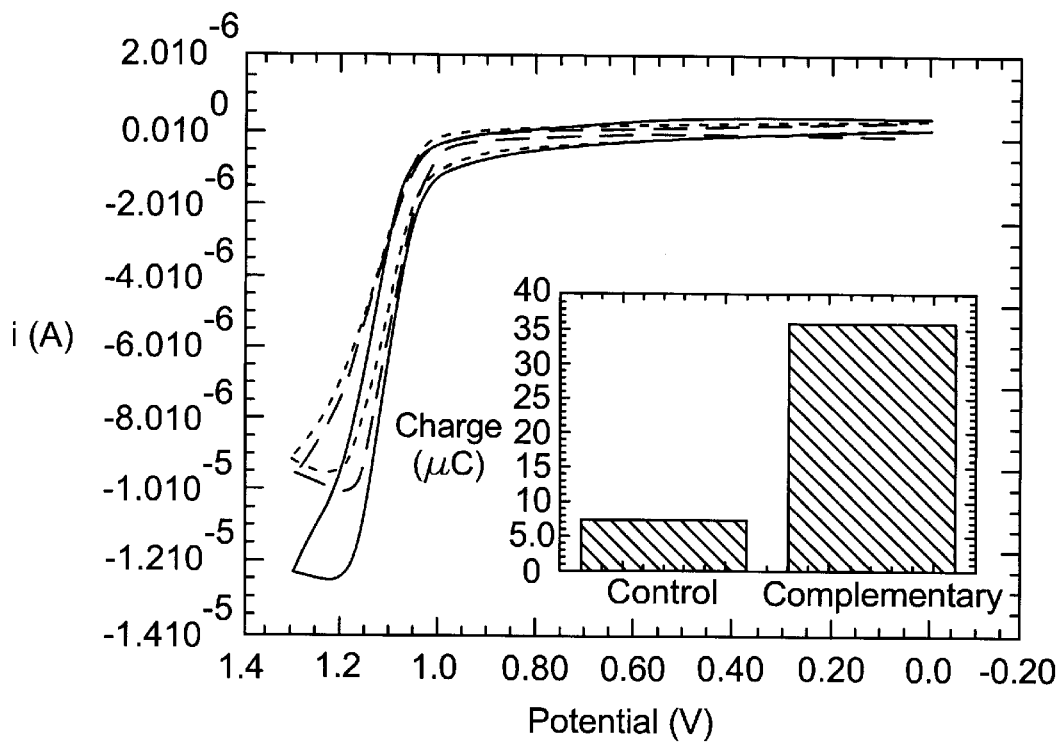
FIGS. 3A–3C. (A) Cyclic voltammograms taken at 25 mV/s of $Ru(bpy)_3^{2+}$(100 $\mu$M) at an ITO polymer-electrode showing the current (i) measured at the electrode with only an inosine-substituted 21-mer probe attached (dotted) and after exposure to 200 $\mu$L solution of 1 nmol of the complementary (solid) and control (dashed) oligonucleotides. Inset: Integrated charge (in microcoulombs, $\mu$C) obtained after subtraction of the current for the unhybridized electrode (dotted) from the current after hybridization to the complementary or control oligonucleotides. (B) Chronoamperometric traces taken with a step in potential from 0 V to 1.3 V with $Ru(bpy)_3^{2+}$(100 $\mu$M) showing current collected at the electrode modified with a 21 -mer probe (dotted) and after exposure to control (dashed) and complementary (solid) oligonucleotides. The dashed and dotted lines appear nearly superimposable on this scale. Inset: Integrated charge in $\mu$C as in FIG. 3A. (C) Data from B replotted on an expanded scale to show the relationship of complementary (solid), control (dashed), and probe only (dotted) scans.
Figure 3B:
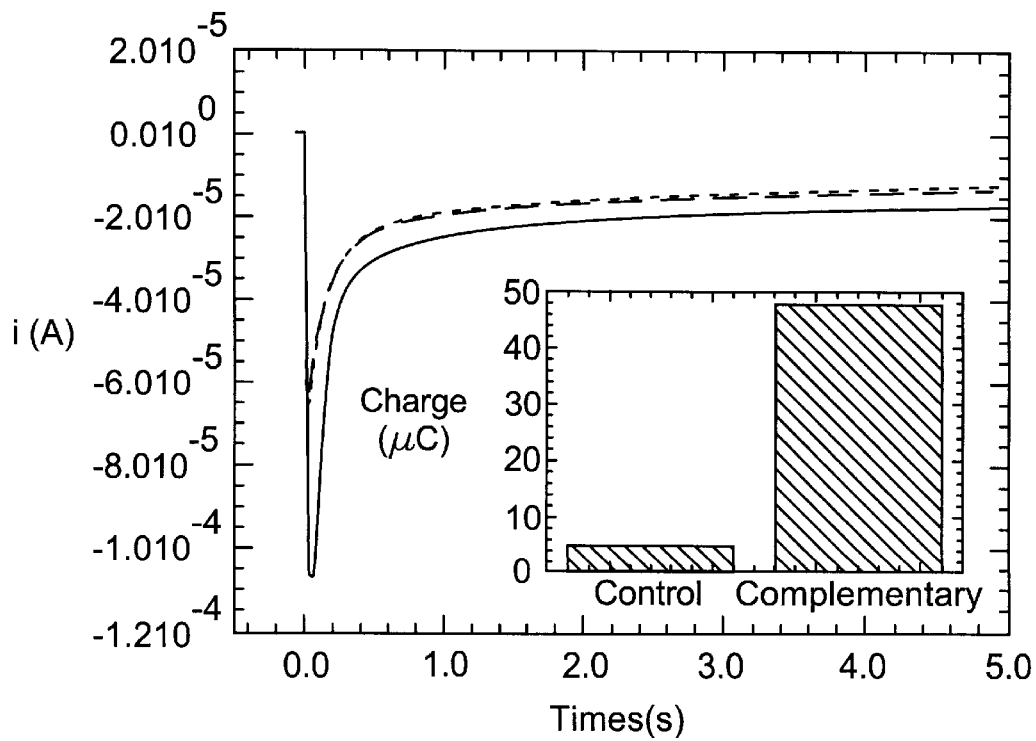
Figure 3C:
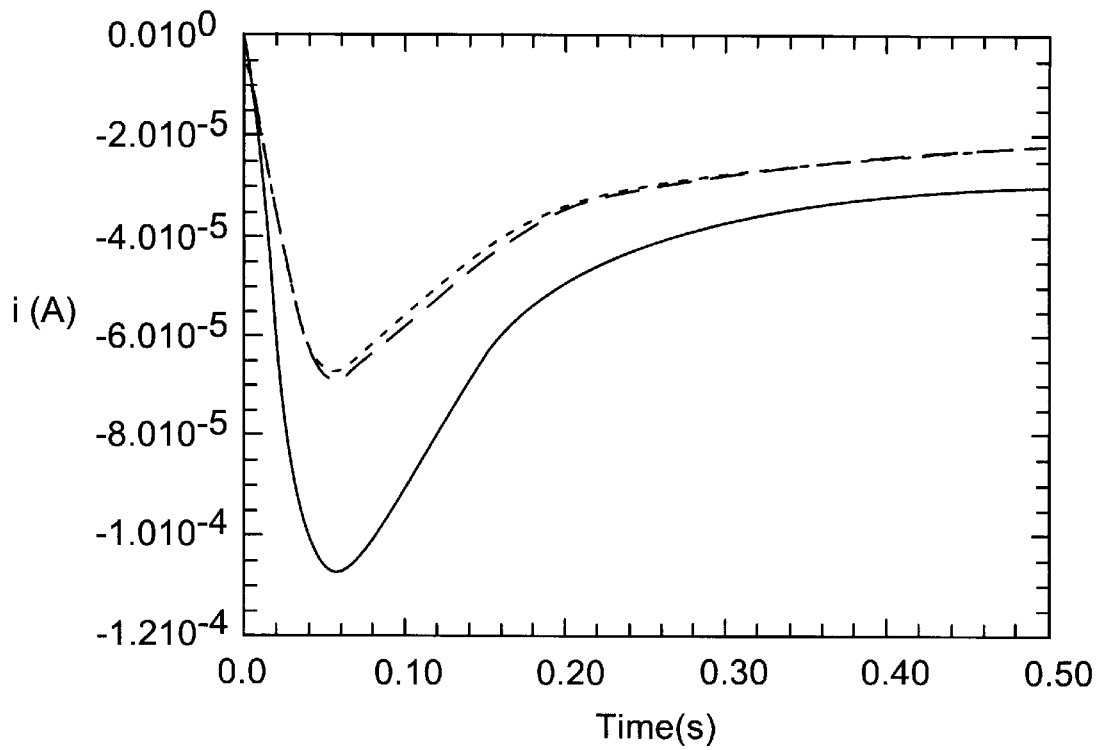

The 21-mer system is also evaluated by chronoamperometry experiments in which the potential is stepped from a resting potential of 0 V to 1.3 V, where Ru(bpy)$_3^{2+}$ is oxidized. The current is collected for 10 s after stepping the potential; the results for the first 5 s are shown in FIG. 3B. As in the cyclic voltammetry experiments, some catalytic current is observed with the probe-modified polymer-electrode (dotted) with a much greater increase after hybridization (solid) than after exposure to the control oligonucleotide (dashed). The quantity of charge collected in FIG. 3B as determined by subtraction of the current at the probe-modified polymer-electrode and integration over the entire time period (inset) is similar to that collected in the cyclic voltammetry experiments. The majority of guanine in the polymer layer is consumed in both amperometry conducted for 10 s and cyclic voltammetry at a scan rate of 25 mV/s. While the insets in FIG. 3 clearly show that in both experiments the total charge is significantly greater for the hybridized sample compared to the control, the chronoamperometry data also show significant enhancements in the instantaneous current, at early times in the catalytic cycle. The chronoamperometry data are shown on an expanded scale in FIG. 3C, where at t=0.5 s there is a 38 $\mu$A enhancement in the hybridized sample while there is only a 2 $\mu$A enhancement for the control.

EXAMPLE 12. Results of Amplification.

Figure 5:
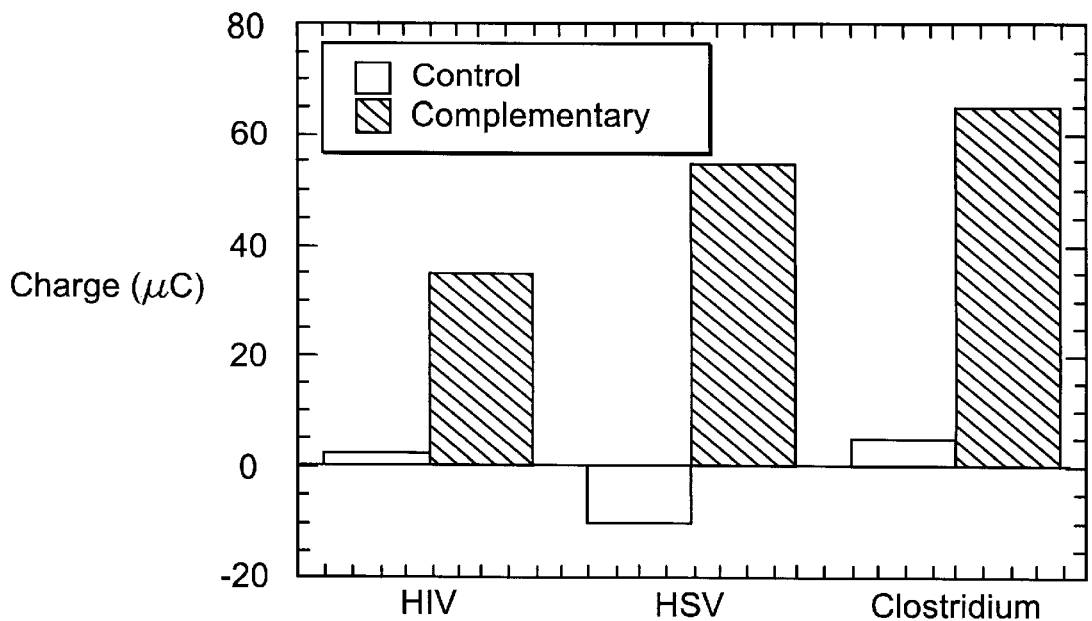
FIG. 5. Integrated charge collected in cyclic voltammetry experiments following hybridization of PCR products from infectious disease agents, using polymer-electrodes. Probes containing sequences complementary to PCR amplified DNA from HIV, Herpes simplex virus (HSV) or *Clostridium perfringens* bacteria (Table 1) were covalently attached to the polymer-electrodes. Control experiments had an unrelated 21-mer ras probe attached to polymer-electrodes. Data were collected after hybridization and analyzed as in FIG. 3A.

The technology is also capable of detecting PCR products of biologically significant length in unpurified amplification reactions. Genomic DNA from HSV and *Clostridium perfringens* is amplified using PCR as described elsewhere (Daube, G. et al., (1994). *J. Appl. Bacteriology* 77, 650–655; Lulitanond, V. et al., (1994). *Mol. Cell Probes* 8, 441–447), and the unpurified PCR reactions are hybridized to the polymer membranes modified with the appropriate probes. Genomic RNA from HIV is amplified by RT-PCR (Martin, W. J. (1994) Infectious Diseases. In *The Polymerase Chain Reaction* (K. B. Mullis, F. Perre and R. A. Gibbs, eds.), pp. 406–417. Berkhauser, Boston) and similarly hybridized. The cyclic voltammograms of the probe-modified and hybridized polymer-electrodes are collected along with the appropriate controls. The charge passed during each voltammogram (in $\mu$C) is determined as in FIG. 3, inset. The bar graph in FIG. 5 shows the differential charge obtained following subtraction of the charge measured at the probe-modified polymer-electrodes from that measured at the hybridized polymer-electrodes. Controls involved exposing polymer membranes modified with the 21-mer ras probe to the unpurified PCR reactions of the HIV, HSV, or *C. perfringens* genomes under the same conditions. An increase in the charge above that for the probe-modified polymer membranes signals either background signal in the control case or a successful hybridization event for the complementary case. In all three cases, the complementary hybridization shows a significant increase in charge when compared to the control hybridization. The charge increase signifies that the HIV, HSV, and *C. perfringens* amplicons successfully hybridize to the probe attached to the polymer membrane. In contrast, little or no residual charge is observed for the controls, indicating a minimal amount of binding of amplicon or other components of the unpurified PCR reaction mixture to the polymer membrane.

EXAMPLE 13. Detection of DNA Using Immobilized Protein.

The enzyme BamH1, which binds DNA having the sequence 5'-GGATCC, is immobilized via carbodiimide coupling on the oxidized carboxylated CYCLOPORE™ membranes activated using either the wet or dry method as discussed above. The polymer membrane with immobilized protein is washed with buffer as above, and contacted with an ITO conductive surface. The polymer-electrode is equilibrated with Ru(bpy)$_3^{2+}$, and the cyclic voltammogram is measured as in the previous examples. There is little catalytic current for the metal complex at the protein-modified polymer-electrode. The polymer layer is then exposed to a solution of DNA in the absence of Mg$^{2+}$ where some of the DNA contains the sequence 5'-GGATCC. The DNA containing the recognition sequence binds to the immobilized BamH1. Another cyclic voltammogram is measured after equilibration with Ru(bpy)$_3^{2+}$, and shows catalytic current in proportion to the amount of DNA bound to the polymer membrane and hence gives the fraction of DNA in the analyte solution that contains the target sequence.

EXAMPLE 14. Detection of DNA Using an Immobilized Small Molecule.

Streptavidin is modified with multiple 3'-aminohexylpolyguanine oligonucleotides using glutaraldehyde-mediated covalent coupling. A synthetic biotin derivative bearing a pendant amino group is conjugated to the oxidized carboxylated CYCLOPORE™ (PET) membrane via a carbodiimide reaction, and the polymer membrane is affixed to the ITO conductive surface. There is little catalytic current for the biotinylated polymer-electrode. The biotinylated polymer membrane is exposed to poly[dG]-labeled streptavidin. The polymer membrane is washed, contacted to the ITO conductive surface and equilibrated with Ru(bpy)$_3^{2+}$. Significant catalytic current is measured in response to the amount of labeled streptavidin bound to the polymer membrane.

EXAMPLE 15. Detection of DNA Using Immobilized Proteins.

The enzyme β-galactosidase is attached to the polymer membrane via a carbodiimide reaction and the methods described in Example 13. A monoclonal antibody to β-galactosidase is obtained and modified with poly[dG] tails as described above for streptavidin. The β-galactosidase-modified polymer membrane is contacted to the ITO conductive surface, equilibrated with Ru(bpy)$_3^{2+}$, and analyzed by cyclic voltammetry. There is little catalytic current for the protein-modified polymer-electrode. The polymer membrane is exposed to the labeled monoclonal antibody, washed and equilibrated with Ru(bpy)$_3^{2+}$. Significant catalytic current is measured in proportion to the amount of bound antibody.

While the invention has been described in connection with a preferred embodiment, it is not intended to limit the scope of the invention to the particular form set forth, but on the contrary, it is intended to cover such alternatives, modifications, and equivalents as may be included within the spirit and scope of the invention as defined by the appended claims.

What is claimed is:

1. A polymer-electrode comprising:
   (a) a substrate having a conductive working surface; and
   (b) a nonconductive outer polymer layer on said conductive working surface, said polymer layer having a plurality of microfluidic reaction openings distributed throughout the layer, and through which layer a transition metal complex can transfer electrons to the conductive working surface.

2. The polymer-electrode according to claim 1, further comprising an oligonucleotide probe attached to the polymer layer.

3. The polymer-electrode according to claim 1, further comprising a protein-binding substance attached to the polymer layer.

4. The polymer-electrode according to claim 1, wherein the polymer layer is activated with a coupling agent.

5. The polymer-electrode according to claim 4, wherein the coupling agent is a carbodiimide.

6. The polymer-electrode according to claim 1, wherein the substrate is selected from the group consisting of metallic substrates and non-metallic substrates.

7. The polymer-electrode according to claim 1, wherein the conductive working surface is indium-tin oxide and the polymer layer is a polyethylene terephthalate.

8. An apparatus comprising:
   (a) a sample container for holding a fluid sample;
   (b) a polymer-electrode in electronic communication with the sample container, said polymer-electrode comprising a substrate having a conductive working surface, and a nonconductive outer polymer layer on the conductive working surface, said polymer layer having a plurality of microfluidic reaction openings, and through which layer a transition metal complex can transfer electrons to the conductive working surface; and
   (c) a potentiostat in electronic communication with the polymer-electrode.

9. A method of determining the presence of a target in a sample, comprising:
   (a) contacting a nonconductive polymer layer with a label-bearing target which is capable of being oxidized in an oxidation-reduction reaction, said polymer layer having a plurality of microfluidic reaction openings and through which layer a transition metal complex can transfer electrons to the conductive working surface as recited in step (e) below, said polymer layer having immobilized thereon a binding molecule capable of binding to the target so that the immobilized binding molecule and the target form a target complex on the polymer layer;
   (b) reacting the target complex with a transition metal complex capable of oxidizing the label-bearing target in an oxidation-reduction reaction;
   (c) detecting the oxidation-reduction reaction;
   (d) determining the presence or absence of the target from the detected oxidation-reduction reaction; and
   (e) contacting the polymer layer with a conductive working surface of a substrate at any time prior to detecting the oxidation-reduction reaction.

10. The method according to claim 9, wherein the sample is selected from the group consisting of: synthetic or natural oligonucleotides, surgical specimens, specimens used for medical diagnostics, specimens used for genetic testing, environmental specimens, food specimens, dental specimens and veterinary specimens.

11. The method of claim 9, wherein the label-bearing target is a nucleic acid containing guanine and the immobilized binding molecule is a nucleic acid hybridizable with said target to form a hybridized target complex.

12. The method according to claim 11, wherein the polymer layer is brought into contact with the conductive working surface of the substrate after reacting the hybridized target complex with the transition metal complex.

13. The method according to claim 11, wherein the sample is selected from the group consisting of: synthetic or natural oligonucleotides, surgical specimens, specimens used for medical diagnostics, specimens used for genetic testing, environmental specimens, food specimens, dental specimens and veterinary specimens.

14. A method of preparing a polymer-electrode, comprising:
   (a) providing a substrate having a conductive working surface;
   (b) preparing a nonconductive polymer layer for attachment thereto of a binding molecule capable of binding to a substance of interest, said polymer layer having a plurality of microfluidic reaction openings, and wherein a transition metal complex can transfer electrons to the conductive working surface through the polymer layer;
   (c) attaching a binding molecule to the polymer layer; and
   (d) contacting the polymer layer to the conductive working surface of the substrate.

15. The method according to claim 14, wherein preparing the polymer layer includes providing of carboxylate moieties.

16. The method according to claim 15, wherein the carboxylate moieties are activated with a coupling agent.

17. The method according to claim 16, wherein the coupling agent is water soluble carbodiimide.

18. The method according to claim 14, wherein the binding molecule for which the polymer layer in step (b) is prepared is an oligonucleotide.

19. The method according to claim 18, further comprising coupling to the polymer-layer an oligonucleotide which hybridizes with a nucleic acid as the substance of interest.

20. A method of determining the presence of a target protein in a sample, comprising:
   (a) providing a protein-binding substance attached to a nonconductive polymer layer having a plurality of microfluidic reaction openings wherein a transition metal complex can transfer electrons through the polymer layer to a conductive working surface when the polymer layer is contacted with the conductive working surface as recited in step (g) below;
   (b) exposing the protein-binding substance to the sample;
   (c) exposing the polymer layer to a second protein-binding substance capable of binding the target protein and which has been modified to contain a label;
   (d) reacting the bound target protein with a transition metal complex capable of oxidizing the label in an oxidation-reduction reaction;
   (e) detecting the oxidation-reduction reaction;
   (f) determining the presence or absence of the protein from the detected oxidation-reduction reaction; and
   (g) contacting the polymer layer with a conductive working surface of a substrate prior to detecting the oxidation-reduction reaction.

21. The method according to claim 20, wherein the polymer layer is brought into contact with the conductive working surface of the substrate after reacting the polymer layer with the transition metal complex.

22. The method according to claim 20, wherein the label on the second protein-binding substance is an oligonucleotide.

23. The polymer-electrode according to claim 3, wherein the protein-binding substance comprises a protein.

24. The apparatus according to claim 8, further comprising an oligonucleotide probe attached to the polymer layer.

25. The apparatus according to claim 8, further comprising a protein-binding substance attached to the polymer layer.

26. The method according to claim 11, further comprising amplifying the target nucleic acid to produce an amplified nucleic acid solution prior to contacting the polymer layer.

27. The method according to claim 14, wherein the binding molecule for which the polymer layer in step (b) is prepared is a protein.

28. The method according to claim 27, further comprising coupling to the polymer-electrode a protein which binds to the substance of interest.

29. A method of determining the presence of a target protein in a sample, comprising:
   (a) providing a binding molecule attached to a nonconductive polymer layer having a plurality of microfluidic reaction openings, wherein a transition metal complex can transfer electrons through the polymer layer to a conductive working surface when the polymer layer is contacted with the conductive working surface as recited in step (f) below;
   (b) forming a bound complex by exposing the binding molecule to a sample that has been modified to contain a label;
   (c) reacting the bound complex with a transition metal complex capable of oxidizing the label in an oxidation-reduction reaction;
   (d) detecting the oxidation-reduction reaction;
   (e) determining the presence or absence of the protein from the detected oxidation-reduction reaction; and
   (f) contacting the polymer layer with a conductive working surface of a substrate prior to detecting the oxidation-reduction reaction.

30. The method of claim 29, wherein the binding molecule is a protein-binding substance.

31. The method of claim 29, wherein the binding molecule is an oligonucleotide.

32. The method according to claim 26, wherein the amplification is carried out by a method selected from the group consisting of polymerase chain reaction, strand displacement amplification, ligase chain reaction, and nucleic acid sequence-based amplification.

33. The method according to claim 26, wherein the polymer layer is brought into contact with the conductive working surface of the substrate after reacting the hybridized target complex with the transition metal complex.

* * * * *

UNITED STATES PATENT AND TRADEMARK OFFICE
CERTIFICATE OF CORRECTION

PATENT NO. : 5,968,745

DATED : October 19, 1999

INVENTOR(S) : Thorp et al.

It is certified that error appears in the above-identified patent and that said Letters Patent is hereby corrected as shown below:

On the Title Page:
Under "Other Publications", in the Du et al. reference (fifth reference on page), please delete "FlUorescent" and insert - - Fluorescent - -.

In the Claims:

Column 2, line 56, please delete "MRNA" and insert - - mRNA - -.

Column 3, line 39, after "(bpy), please delete ",".

Column 3, line 55, please delete "21 –mer" and insert - - 21-mer - - .

Column 8, line 21, please delete "methylaminomethyluridine" and insert - - methylaminomethyluridine".

Column 9, line 39, please delete "(($CO2)_2$-bpy)" and insert - - (($CO_2)_2$-b[py) - -.

Column 9, line 54, please delete "4,4', 4" and insert - - 4,4',4 - -.

Column 9, line 62, please delete "4,7-dinitro- 1,10" and insert - - 4,7-dinitro-1,10 - -.

Column 9, line 64, please delete "diphenyl- 1,10" and insert - - diphenyl-1,10 - -.

Column 12, line 57, please delete "betweens" and insert - - between - -.

Column 13, line 26, please delete "Ru (bpy)" and insert - - Ru(bpy) - -..

Column 15, line 3, please delete "synthetic 21 –mer" and insert - - synthetic 21-mer - -.

Column 18, line 50, please delete "Ru(bpy),$^{2+}$ in" and insert - - Ru(bpy)$_3^{2+}$ in - -.

UNITED STATES PATENT AND TRADEMARK OFFICE
CERTIFICATE OF CORRECTION

PATENT NO. : 5,968,745

DATED : October 19, 1999

INVENTOR(S) : Thorp et al.

It is certified that error appears in the above-identified patent and that said Letters Patent is hereby corrected as shown below:

Column 18, line 63, please delete "21 –mer" and insert - - 21-mer - -.

Column 19, line 38, please delete "Perre" and insert - - Ferre - -.

Signed and Sealed this

Twenty-seventh Day of March, 2001

Attest:

NICHOLAS P. GODICI

Attesting Officer

Acting Director of the United States Patent and Trademark Office